US007524856B2

(12) United States Patent
Hossain et al.

(10) Patent No.: US 7,524,856 B2
(45) Date of Patent: Apr. 28, 2009

(54) TRICYCLIC SPIRODERIVATIVES AS MODULATORS OF CHEMOKINE RECEPTOR ACTIVITY

(75) Inventors: Nafizal Hossain, Lund (SE); Svetlana Ivanova, Lund (SE)

(73) Assignee: AstraZeneca AB (SE)

( * ) Notice: Subject to any disclaimer, the term of this patent is extended or adjusted under 35 U.S.C. 154(b) by 115 days.

(21) Appl. No.: 10/583,468

(22) PCT Filed: Dec. 20, 2004

(86) PCT No.: PCT/SE2004/001938

§ 371 (c)(1),
(2), (4) Date: Jun. 20, 2006

(87) PCT Pub. No.: WO2005/061499

PCT Pub. Date: Jul. 7, 2005

(65) Prior Publication Data

US 2007/0099945 A1  May 3, 2007

(30) Foreign Application Priority Data

Dec. 22, 2003  (SE)  .................................. 0303541

(51) Int. Cl.
*A61K 31/438* (2006.01)
*C07D 491/107* (2006.01)
(52) U.S. Cl. .................. 514/278; 546/17; 548/409; 514/409
(58) Field of Classification Search ................. 514/278, 514/409; 546/17; 548/409
See application file for complete search history.

(56) References Cited

U.S. PATENT DOCUMENTS

| 4,010,201 | A | 3/1977 | Lednicer |
| 4,263,317 | A | 4/1981 | Martin et al. |
| 5,962,462 | A | 10/1999 | Mills et al. |
| 2005/0245741 | A1 | 11/2005 | Hossain et al. |
| 2006/0252751 | A1 | 11/2006 | Xue et al. |
| 2007/0021498 | A1 | 1/2007 | Hossain |
| 2007/0099945 | A1 | 5/2007 | Hossain et al. |
| 2007/0123543 | A1 | 5/2007 | Hossain et al. |
| 2007/0129393 | A1 | 6/2007 | Baxter et al. |
| 2007/0203229 | A1 | 8/2007 | Hossain |
| 2007/0203230 | A1 | 8/2007 | Hossain |
| 2007/0249648 | A1 | 10/2007 | Bladh et al. |
| 2008/0167332 | A1 | 7/2008 | Mensonides-Harsema et al. |

FOREIGN PATENT DOCUMENTS

| EP | 0 004 951 B1 | 10/1979 |
| EP | EP 0004952 | 10/1979 |
| EP | 0417631 | 3/1991 |
| EP | 0722941 | 7/1996 |
| EP | 1061076 | 12/2000 |
| WO | WO 92/10096 | 6/1992 |
| WO | WO 96/36625 | 11/1996 |
| WO | WO 98/25605 | 6/1998 |
| WO | WO 98/31364 | 7/1998 |
| WO | WO 00/14086 | 3/2000 |
| WO | WO 01/30780 | 5/2001 |
| WO | WO 01/64213 A1 | 9/2001 |
| WO | WO 01/98273 | 12/2001 |
| WO | WO 02/102387 A1 | 12/2002 |
| WO | WO 03/037271 | 5/2003 |
| WO | WO 2004/005295 A1 | 1/2004 |
| WO | WO 2004/041279 | 5/2004 |
| WO | WO 2005/037814 | 4/2005 |
| WO | WO 2005/040167 | 5/2005 |
| WO | WO 2005/049620 | 6/2005 |
| WO | WO 2005/054249 | 6/2005 |
| WO | WO 2005/061499 | 7/2005 |
| WO | WO 2005/092895 | 10/2005 |
| WO | WO 2008/010765 | 1/2008 |

OTHER PUBLICATIONS

Pujol et al., "Novel tricyclic spiropiperidines. Synthesis and adrenergic activity of spiro[1,3-benzodioxolopiperidines] and spiro[1,3-benzodioxanepiperidines]", *Eur J Med Chem* 31:889-894 (1996).
Mehrotra et al., "Spirocyclic Nonpeptide Glycoprotein IIb-IIIa Antagonists. Part 3: Synthesis and SAR of Potent and Specific 2,8-Diazaspiro[4.5]decanes", Bioorganic & Medicinal Chemistry Letters 12:1103-1107 (2002).
Chen et al., "Heterodimerization and cross-desensitization between the μ-opioid receptor and the chemokine CCR5 receptor", *Eur. J. Pharmacol.* 483:175-186 (2004).
Dorwald F.Z. *Side Reactions in Organic Synthesis*. Wiley: VCH, Weinheim, 2005. p. IX of Preface.
Godessart N., "Chemokine Receptors: Attractive Targets for Drug Discovery", *Ann. N.Y. Acad. Sci.* 1051:647-657 (2005).
Knochel et al., "Highly Functionalized Organomagnesium Reagents Prepared through Haolgen-Metal Exchange", *Angew. Chem. Int. Ed.* 42:4302-4320 (2003).
Li J.J. "Grignard reaction." in: *Name Reactions: A Collection of Detailed Reaction Mechanisms* Third Expanded Edition Springer 2006, pp. 271-272.
Brown et al., "Novel CCR1 antagonists with improved metabolic stability", *Bioorg. Med. Chem. Lett.* 14:2175-2179 (2004).
Martin et al., "Do Structurally Similar Molecules Have Similar Biological Activity?", *J. Med. Chem.* 45:4350-4358 (2002).
Pozharskii et al., *Heterocycles in Life and Society*. Wiley, 1997, pp. 1-6.
Thoma et al., "Orally Bioavailable Competitive CCR5 Antagonists", *J. Med. Chem.* 47:1939-1955 (2004).
Thomson et al., *The Cytokine Handbook*, 4th ed. New York, Academic Press, 2003, pp. 1084-1087.
Ting et al., "The synthesis of substituted bipiperidine amide compounds as CCR3 ligands: Antagonist versus agonists", *Bioorg. Med. Chem. Lett.* 15:3020-3023 (2005).
Xie et al., "Identification of novel series of human CCR1 antagonists", *Bioorg. Med. Chem. Lett.* 18:2215-2221 (2008).

*Primary Examiner*—Charanjit S Aulakh
(74) *Attorney, Agent, or Firm*—Fish & Richardson P.C.

(57) ABSTRACT

The invention provides compounds of formula (I) wherein m, $R^1$, n, $R^2$, q, p, X, Y, $R^3$, $R^4$, t and, $R^5$ are as defined in the specification, processes for their preparation, pharmaceutical compositions containing them and their use in therapy.

17 Claims, No Drawings

TRICYCLIC SPIRODERIVATIVES AS MODULATORS OF CHEMOKINE RECEPTOR ACTIVITY

CROSS-REFERENCE TO RELATED APPLICATIONS

This application is a national phase application under 35 U.S.C. §371 of PCT International Application No. PCT/SE2004/001938, filed Dec. 20, 2004, which claims priority to Swedish Application Serial No. 0303541-7, filed Dec. 22, 2003.

The present invention relates to novel compounds, processes for their preparation, pharmaceutical compositions containing them and their use in therapy. In particular, the invention relates to novel spirocyclic compounds, their preparation and use.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2). The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins $1\alpha$ and $1\beta$ (MIP-$1\alpha$ and MIP-$1\beta$).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Spiro(dihydrobenzofuran)piperidines and pyrrolidines having activity as analgesics and tranquillising agents are described in U.S. Pat. No. 4,166,119. Spiro(2,3-dihydrobenzofuran-2,4-piperid-1-yl)derivatives of interest inter alia as antipsychotic and cerebral ischaemic agents are described in EP 0 351 282 B.

In accordance with the present invention, there is provided a compound of formula (I)

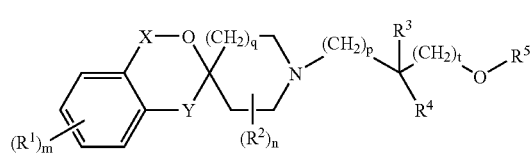

(I)

wherein
m is 0, 1, 2, 3 or 4;

each $R^1$ independently represents halogen, cyano, hydroxyl, $C_1$-$C_6$ alkyl, $C_1$-$C_6$ haloalkyl, $C_1$-$C_6$ alkoxy, $C_1$-$C_6$ alkylsulphonyl or sulphonamido (—$SO_2NH_2$);

X represents a bond or —$CH_2$— and Y represents a bond or —$CH_2$—, provided that X and Y do not both simultaneously represent a bond or —$CH_2$—;

n is 0, 1 or 2;

each $R^2$ independently represents halogen, $C_1$-$C_6$ alkyl or $C_1$-$C_6$ haloalkyl;

q is 0 or 1;

p is 0, 1 or 2;

$R^3$ represents a group selected from halogen, $NR^6R^7$, carboxyl or $C_1$-$C_6$ alkyl wherein said $C_1$-$C_6$ alkyl group is optionally substituted by one or more halogen, amino, hydroxyl, $C_1$-$C_6$ alkoxy, N—($C_1$-$C_6$ alkyl)amino, N,N-di-($C_1$-$C_6$ alkyl)amino, carboxy or carbamoyl;

$R^4$ represents hydrogen, $C_1$-$C_6$ alkyl, $C_1$-$C_6$ haloalkyl or halogen;

t is 0, 1 or 2, provided that p and t are not both 0;

$R^5$ represents a saturated or unsaturated 5- to 10-membered ring system which ring system may comprise at least one ring heteroatom selected from nitrogen, oxygen and sulphur, the ring system being optionally substituted by one or more substituents independently selected from halogen, cyano, oxo, nitro, hydroxyl, carboxyl, —C(O)H, —$NR^8R^9$, —C(O)$NR^{10}R^{11}$, —NHC(O)$R^{12}$, —$NHSO_2R^{13}$, —$SO_2NR^{14}R^{15}$, —NHC(O)$NR^{16}R^{17}$, a group selected from $C_1$-$C_6$ alkyl, $C_2$-$C_6$ alkenyl, $C_2$-$C_6$ alkynyl, $C_1$-$C_6$ alkoxy, $C_1$-$C_6$ alkylthio, $C_1$-$C_6$ alkylsulphonyl, $C_1$-$C_6$ haloalkyl, $C_1$-$C_6$ alkylcarbonyl, phenylcarbonyl, $C_3$-$C_6$ cycloalkyl, phenyl and a saturated or unsaturated 5- to 6-membered heterocyclic ring comprising at least one ring heteroatom selected from nitrogen, oxygen and sulphur, each group being optionally substituted by one or more substituents independently selected from halogen, cyano, hydroxyl, carboxyl, $C_1$-$C_6$ alkyl, C3-C6 cycloalkyl, $C_1$-$C_6$ alkoxy and $C_1$-$C_6$ alkoxycarbonyl;

$R^6$ and $R^7$ each independently represent hydrogen or a group selected from $C_1$-$C_6$ alkyl and $C_1$-$C_6$ alkylcarbonyl, each of which may be optionally substituted by one or more substituents selected from halogen, amino, hydroxyl, $C_1$-$C_6$ alkoxy, N—($C_1$-$C_6$ alkyl)amino, N,N-di-($C_1$-$C_6$ alkyl)amino, carboxy, carbamoyl or $C_1$-$C_6$ alkoxycarbonyl, or R6 and R7 together with the nitrogen atom to which they are attached form a 4- to 7-membered saturated heterocyclic ring which may be optionally substituted by one or more substituent selected from halogen, amino, hydroxyl, $C_1$-$C_6$ alkoxy, N—($C_1$-$C_6$ alkyl)amino, N,N-di-($C_1$-$C_6$ alkyl)amino, carboxy, carbamoyl or $C_1$-$C_6$ alkoxycarbonyl;

$R^8$, $R^9$, $R^{10}$, $R^{11}$ each independently represent hydrogen or a group selected from $C_1$-$C_6$ alkyl or $C_3$-$C_6$ cycloalkyl, each group being optionally substituted by one or more substituents independently selected from halogen, amino, hydroxyl, $C_1$-$C_6$ alkoxy, N—($C_1$-$C_6$ alkyl)amino, N,N-di-($C_1$-$C_6$ alkyl)amino, carboxy or carbamoyl; or $R^{10}$ and $R^{11}$, together with the nitrogen atom to which they are attached form a 4- to 7-membered saturated heterocyclic ring which may be optionally substituted with at least one substituent selected from halogen, amino, hydroxyl, $C_1$-$C_6$ alkoxy, N—($C_1$-$C_6$ alkyl)amino, N,N-di-($C_1$-$C_6$ alkyl)amino, carboxy or carbamoyl;

$R^{12}$ represents hydrogen or a group selected from $C_1$-$C_6$ alkyl or $C_3$-$C_6$ cycloalkyl, each group being optionally substituted by one or more substituents independently selected from halogen, amino, hydroxyl, $C_1$-$C_6$ alkoxy, N—($C_1$-$C_6$ alkyl)amino, N,N-di-($C_1$-$C_6$ alkyl)amino, carboxy or carbamoyl;

$R^{13}$ represents a group selected from $C_1$-$C_6$ alkyl or $C_3$-$C_6$ cycloalkyl, each group being optionally substituted by one or more substituents independently selected from halogen, amino, hydroxyl, $C_1$-$C_6$ alkoxy, N—($C_1$-$C_6$ alkyl)amino, N,N-di-($C_1$-$C_6$ alkyl)amino, carboxy or carbamoyl;

$R^{14}$, $R^{15}$, $R^{16}$ and $R^{17}$ each independently represent hydrogen or a group selected from $C_1$-$C_6$ alkyl or $C_3$-$C_6$ cycloalkyl, each group being optionally substituted by one or more substituents independently selected from halogen, amino, hydroxyl, $C_1$-$C_6$ alkoxy, N—($C_1$-$C_6$ alkyl)amino, N,N-di-($C_1$-$C_6$ alkyl)amino, carboxy or carbamoyl; or $R^{14}$ and $R^{15}$, or $R^{16}$ and $R^{17}$, together with the nitrogen atom to which they are attached each independently form a 4- to 7-membered saturated heterocyclic ring which may be optionally substituted with at least one substituent selected from halogen, amino, hydroxyl, $C_1$-$C_6$ alkoxy, N—($C_1$-$C_6$ alkyl)amino, N,N-di-($C_1$-$C_6$ alkyl)amino, carboxy or carbamoyl;

or a pharmaceutically acceptable salt or solvate thereof.

Unless otherwise indicated, the term 'alkyl' when used alone or in combination, refers to a straight chain or branched chain alkyl moiety. A $C_1$-$C_6$ alkyl group has from one to six carbon atoms including methyl, ethyl, n-propyl, isopropyl, tert-butyl, n-pentyl, n-hexyl and the like. References to '$C_1$-$C_4$ alkyl' will be understood accordingly to mean a straight or branched chain alkyl moiety having from 1 to 4 carbon atoms. References to individual alkyl groups such as "propyl" are specific for the straight-chain version only, references to individual branched-chain alkyl groups such as "isopropyl" are specific for the branched-chain version only.

Analogously, the terms '$C_1$-$C_6$ alkoxy' and '$C_1$-$C_4$ alkoxy', when used alone or in combination, will be understood to refer to straight or branched chain groups having from one to six or from one to four carbon atoms respectively and includes such groups as methoxy, ethoxy, propoxy, isopropoxy, n-butoxy, isobutoxy, n-pentoxy or n-hexoxy.

A '$C_2$-$C_6$ alkenyl' group refers to a straight or branched chain group having from two to six carbon atoms such as vinyl, isopropenyl, allyl and but-2-enyl. A $C_2$-$C_6$ alkynyl group is suitably ethynyl, 1-propynyl and propyn-2-yl.

The term 'cycloalkyl', when used alone or in combination, refers to a saturated alicyclic moiety having from three to six carbon atoms and includes, for example, cyclopropyl, cyclobutyl, cyclopentyl, cyclohexyl. A $C_3$-$C_6$ cycloalkylmethyl group is suitably cyclopropylmethyl, cyclobutylmethyl, cyclopentylmethyl or cyclohexylmethyl.

As used herein, the term 'halogen' includes fluorine, chlorine, bromine and iodine.

A haloalkyl substituent group will comprise at least one halogen atom, for example one, two, three, four or five halogen atoms. Suitable values include trifluoromethyl or pentafluoroethyl.

A $C_1$-$C_6$ alkysulphonyl group is suitably a methylsulphonyl, ethylsulphonyl, n-propylsulphonyl, isopropylsulphonyl, n-butylsulphonyl, isobutylsulphonyl, tert-butylsulphonyl, n-pentylsulphonyl or n-hexylsulphonyl.

Suitable values for a $C_1$-$C_6$ alkylthio group include methylthio, ethylthio, n-propylthio, isopropylthio, n-butylthio, isobutylthio, tert-butylthio, n-pentylthio or n-hexylthio.

Examples of N—($C_1$-$C_6$ alkyl)amino groups include methylamino and ethylamino. Examples of N,N-di-($C_1$-$C_6$ alkyl)amino groups include di-N-methylamino, di-N-ethylamino and N-ethyl-N-methylamino.

A $C_1$-$C_6$ alkoxycarbonyl group is suitably methoxycarbonyl, ethoxycarbonyl, n- and t-butoxycarbonyl.

Examples of $C_1$-$C_6$ alkylcarbonyl groups include methylcarbonyl, ethylcarbonyl, n-propylcarbonyl, isopropylcarbonyl, n-butylcarbonyl, isobutylcarbonyl, tert-butylcarbonyl, n-pentylcarbonyl or n-hexylcarbonyl 'Optionally substituted' is used herein to indicate optional substitution by the group or groups specified at any suitable available position.

In the ring substituted by $R^2$, $R^2$ may be attached to any suitable ring carbon atom including the carbon atom of $(CH_2)_q$ A 'heteroatom' is a nitrogen, sulphur or oxygen atom. Where rings include nitrogen atoms, these may be substituted as necessary to fulfil the bonding requirements of nitrogen or they may be linked to the rest of the structure by way of the nitrogen atom. Nitrogen atoms may also be in the form of N-oxides. Sulphur atoms may be in the form of S, S(O) or $SO_2$.

A 'saturated or unsaturated 5- to 10-membered ring system which ring system may comprise at least one ring heteroatom selected from nitrogen, oxygen and sulphur' will be understood to refer to a mononcyclic or polycyclic (for example, bicyclic), alicyclic or aromatic ring, carbocyclic or heterocyclic ring system containing from 5 to 10 ring atoms. Unless otherwise specified, the heterocyclic ring may be carbon or nitrogen linked. Examples of suitable ring systems include one or more of cyclopentyl, cyclohexyl, phenyl, bicyclo[2.2.1]heptyl, cyclopentenyl, cyclohexenyl, pyrrolidinyl, piperidinyl, piperazinyl, morpholinyl, thiomorpholinyl, diazabicyclo[2.2.1]hept-2-yl, naphthyl, benzofuranyl, benzothienyl, benzodioxolyl, isoquinolinyl, quinolinyl, 1,2-dihydroquinolinyl, 1,2,3,4-tetrahydroquinolinyl, 2,3-dihydrobenzoxazinyl, quinazolinyl, 1,2,3,4-tetrahydroquinazolinyl, 2,3-dihydrobenzofuranyl, pyrazolyl, pyrazinyl, thiazolidinyl, indanyl, thienyl, isoxazolyl, pyridazinyl, thiadiazolyl, pyrrolyl, furanyl, thiazolyl, indolyl, imidazolyl, pyrimidinyl, benzimidazolyl, triazolyl, tetrazolyl and pyridinyl.

Where reference is made to a saturated or unsaturated 5- to 6-membered heterocyclic ring, it will be understood that this refers to alicyclic or aromatic rings containing five or six ring atoms, representative examples of which are listed above.

A '4- to 7-membered saturated heterocyclic ring' refers to a saturated monocyclic ring system having from 4 to 7 ring atoms in which one or more ring carbons is replaced by a heteroatom selected from nitrogen, oxygen and sulphur. Unless otherwise specified, the heterocyclic ring may be carbon or nitrogen linked. Examples include pyrrolidinyl, piperidinyl, morpholinyl, tetrahydrofuranyl and piperazinyl.

m is suitably 2, 3 or 4 but is preferably 0 or 1.

$R^1$ may be cyano, hydroxyl, $C_1$-$C_6$, preferably $C_1$-$C_4$, alkyl (for example, methyl, ethyl, n-propyl, isopropyl, n-butyl, isobutyl, tert-butyl, n-pentyl or n-hexyl), $C_1$-$C_6$, preferably $C_1$-$C_4$, alkoxy (for example, methoxy, ethoxy, n-propoxy, isopropoxy, n-butoxy, isobutoxy, tert-butoxy, n-pentoxy or n-hexoxy), $C_1$-$C_6$, preferably $C_1$-$C_4$, alkylsulphonyl (for example, methylsulphonyl, ethylsulphonyl, n-propylsulphonyl, isopropylsulphonyl, n-butylsulphonyl, isobutylsulphonyl, tert-butylsulphonyl, n-pentylsulphonyl or n-hexylsulphonyl) or sulphonamido but is preferably halogen (e.g. chlorine, fluorine, bromine or iodine) or $C_1$-$C_6$, preferably $C_1$-$C_4$, haloalkyl (for example, trifluoromethyl or pentafluoroethyl).

In one embodiment, each $R^1$ independently represents halogen, especially fluorine or chlorine.

In another, preferred embodiment, m is 1 and $R^1$ represents halogen, especially fluorine or chlorine.

X may represent —CH$_2$— but preferably X represents a bond and Y represents —CH$_2$—.

Suitably each R$^2$ independently may represent halogen (e.g. chlorine, fluorine, bromine or iodine), C$_1$-C$_6$, preferably C$_1$-C$_4$, alkyl (e.g. methyl, ethyl, n-propyl, isopropyl, n-butyl, isobutyl, tert-butyl, n-pentyl or n-hexyl) or C$_1$-C$_6$, preferably C$_1$-C$_4$, haloalkyl (e.g. trifluoromethyl or pentafluoroethyl).

n may be 2 but is preferably 0 or 1, especially 0.

In another embodiment, n is 1 and R$^2$ represents halogen, especially fluorine;

q is preferably 1

In one embodiment, p is 0.

t is preferably 1

R$^3$ may suitably be halogen (for example, fluorine, chlorine, bromine or iodine), —NR$^6$R$^7$, carboxyl or C$_1$-C$_6$, preferably C$_1$-C$_4$, alkyl (such as methyl, ethyl, n-propyl, isopropyl, n-butyl, isobutyl, tert-butyl, n-pentyl or n-hexyl) optionally substituted by one or more (for example, one, two, three or four) substituents independently selected from halogen, amino, hydroxyl, C$_1$-C$_6$, preferably C$_1$-C$_4$, alkoxy (for example, methoxy, ethoxy, n-propoxy, isopropoxy, n-butoxy, isobutoxy, tert-butoxy, n-pentoxy or n-hexoxy), N—(C$_1$-C$_6$ alkyl)amino (such as methylamino and ethylamino), N,N-di-(C$_1$-C$_6$ alkyl)amino (such as di-N-methylamino, di-N-ethylamino and N-ethyl-N-methylamino), carboxy or carbamoyl.

In an embodiment, R$^3$ represents halogen (preferably fluorine or chlorine), —NR$^6$R$^7$ or C$_1$-C$_6$, preferably C$_1$-C$_4$, alkyl (especially methyl) optionally substituted by one or two substituents selected from halogen, amino or hydroxyl.

In a further embodiment, R$^3$ represents methyl, chlorine, —NH$_2$, —NHMe, —NMe$_2$, —NHCOCH$_3$ or —CH$_2$NH$_2$ R$^4$ may suitably represent halogen, or optionally substituted C$_1$-C$_6$ alkyl but preferably R$^4$ represents hydrogen.

R$^5$ may be a saturated or unsaturated 5- to 10-membered ring system which ring system may comprise at least one ring heteroatom (for example, one, two, three or four ring heteroatoms independently) selected from nitrogen, oxygen and sulphur and which may be optionally substituted one or more substituents (for example, one, two or three substituents) independently selected from halogen, cyano, oxo, nitro, hydroxyl, carboxyl, —C(O)H, —NR$^8$R$^9$, —C(O)NR$^{10}$R$^{11}$, —NHC(O)R$^{12}$, —NHSO$_2$R$^{13}$, —SO$_2$NR$^{14}$R$^{15}$, —NHC(O)NR$^{16}$R$^{17}$, a group selected from C$_1$-C$_6$ alkyl, C$_2$-C$_6$ alkenyl, C$_2$-C$_6$ alkynyl, C$_1$-C$_6$ alkoxy, C$_1$-C$_6$ alkylthio, C$_1$-C$_6$ alkylsulphonyl, C$_1$-C$_6$ haloalkyl, C$_1$-C$_6$ alkylcarbonyl, phenylcarbonyl, C$_3$-C$_6$ cycloalkyl, phenyl and a saturated or unsaturated 5- to 6-membered heterocyclic ring comprising at least one ring heteroatom selected from nitrogen, oxygen and sulphur, each group being optionally substituted by one or more substituents independently selected from halogen, cyano, hydroxyl, carboxyl, C$_1$-C$_6$ alkyl, C$_1$-C$_6$ alkoxy and C$_1$-C$_6$ alkoxycarbonyl.

In one embodiment, R$^5$ is a mononcyclic or polycyclic (for example, bicyclic) unsaturated ring system containing from 5 to 10, preferably from 6 to 10, ring atoms which ring system may comprise one or two ring heteroatoms independently selected from nitrogen and oxygen (e.g. quinolinyl, 1,2-dihydroquinolinyl, 1,2,3,4-tetrahydroquinolinyl, 2,3-dihydrobenzoxazinyl, 1,2,3,4-tetrahydroquinazolinyl, phenyl, naphthyl, pyridinyl, benzofuranyl, pyrimidinyl, isoquinolinyl and quinazolinyl), the ring system being optionally substituted as recited above.

In a further embodiment, R$^5$ is a mononcyclic or polycyclic (for example, bicyclic) unsaturated carbocyclic ring system containing from 5 to 10, preferably from 6 to 10, ring atoms, the ring system being optionally substituted with one, two or three substituents as recited above.

In a particular embodiment, R$^5$ represents phenyl optionally substituted with one or two substituents independently selected from —NHC(O)R$^{12}$, —NHC(O)NR$^{16}$R$^{17}$, hydroxyl or C$_1$-C$_6$ alkoxy.

In a further particular embodiment, R$^5$ represents phenyl optionally substituted with one, two or three substituents independently selected from halogen, hydroxyl, or carboxyl.

In a further embodiment, R$^5$ is a bicyclic unsaturated ring system containing 10 ring atoms, the ring system being substituted with one or two ring heteroatoms independently selected from nitrogen and oxygen, the ring system being optionally substituted with oxo.

R$^6$ and R$^7$ each independently may represent C$_1$-C$_6$, preferably C$_1$-C$_4$, alkyl, optionally substituted by one or more substituents as recited above, or R6 and R7 together with the nitrogen atom to which they are attached form a 4- to 7-membered saturated heterocyclic ring which may be optionally substituted with at least one substituent as recited above, but preferably R$^6$ and R$^7$ each independently represent hydrogen or C$_1$-C$_6$ alkylcarbonyl optionally substituted by one or two substituents as recited above.

In an embodiment of the invention R$^8$ and R$^9$ each independently represent hydrogen or a group selected from C$_1$-C$_6$, preferably C$_1$-C$_4$, alkyl or C$_3$-C$_6$ cycloalkyl, optionally substituted by one or two substituents independently selected from halogen or C$_1$-C$_6$ alkoxy.

In another embodiment, R$^{10}$ and R$^{11}$ each independently represent hydrogen or C$_1$-C$_6$ alkyl or C$_3$-C$_6$ cycloalkyl, optionally substituted by one or two substituents independently selected from halogen, amino, hydroxyl, C$_1$-C$_6$ alkoxy, N—(C$_1$-C$_6$ alkyl)amino, N,N-di-(C$_1$-C$_6$ alkyl)amino, carboxy or carbamoyl; or R$^{10}$ and R$^{11}$ together with the nitrogen atom to which they are attached form a 4- to 7-membered saturated heterocyclic ring which may be optionally substituted with at least one substituent as recited above.

R$^{12}$ and R$^{13}$ each independently preferably represent C$_1$-C$_6$ alkyl or C$_3$-C$_6$ cycloalkyl, optionally substituted by one or two substituents independently selected from halogen, amino, hydroxyl, C$_1$-C$_6$ alkoxy, N—(C$_1$-C$_6$ alkyl)amino, N,N-di-(C$_1$-C$_6$ alkyl)amino, carboxy or carbamoyl.

R$^{14}$ and R$^{15}$ each independently preferably represent hydrogen or C$_1$-C$_6$ alkyl or C$_3$-C$_6$ cycloalkyl, optionally substituted by one or two substituents independently selected from halogen, amino, hydroxyl, C$_1$-C$_6$ alkoxy, N—(C$_1$-C$_6$ alkyl)amino, N,N-di-(C$_1$-C$_6$ alkyl)amino, carboxy or carbamoyl, or R$^{14}$ and R$^{15}$ together with the nitrogen atom to which they are attached form a 4- to 7-membered saturated heterocyclic ring which may be optionally substituted with at least one substituent as recited above.

In another embodiment, R$^{16}$ and R$^{17}$ each independently represent hydrogen or C$_1$-C$_6$ alkyl or C$_3$-C$_6$ cycloalkyl, optionally substituted by one or two substituents independently selected from halogen, amino, hydroxyl, C$_1$-C$_6$ alkoxy, N—(C$_1$-C$_6$ alkyl)amino, N,N-di-(C$_1$-C$_6$ alkyl)amino, carboxy or carbamoyl;, or R$^{16}$ and R$^{17}$ together with the nitrogen atom to which they are attached form a 4- to 7-membered saturated heterocyclic ring which may be optionally substituted with at least one substituent as recited above.

In one preferred group of compounds of formula (I) according to the invention, m is 0 or 1;

R$^1$ is halogen;

X represents a bond and Y represents —CH$_2$—;

q is 1;

n is 0;

R³ is halogen, —NR⁶R⁷ or C₁-C₆ alkyl optionally substituted by one or two substituents selected from halogen, amino or hydroxyl;

R⁴ is hydrogen;

R⁵ is an unsaturated ring system containing from 5 to 10 ring atoms which ring system may comprise one or two ring heteroatoms independently selected from nitrogen and oxygen and which is optionally substituted by one or more substituents independently selected from halogen, cyano, oxo, nitro, hydroxyl, carboxyl, —C(O)H, —NR⁸R⁹, —C(O)NR¹⁰R¹¹, —NHC(O)R¹², —NHSO₂R¹³, —SO₂NR¹⁴R¹⁵, —NHC(O)NR¹⁶R¹⁷, a group selected from C₁-C₆ alkyl, C₂-C₆ alkenyl, C₂-C₆ alkynyl, C₁-C₆ alkoxy, C₁-C₆ alkylthio, C₁-C₆ alkylsulphonyl, C₁-C₆ haloalkyl, C₁-C₆ alkylcarbonyl, phenylcarbonyl, C₃-C₆ cycloalkyl, phenyl and a saturated or unsaturated 5- to 6-membered heterocyclic ring comprising at least one ring heteroatom selected from nitrogen, oxygen and sulphur, each group being optionally substituted by one or more substituents independently selected from halogen, cyano, hydroxyl, carboxyl, C₁-C₆ alkyl, C₁-C₆ alkoxy and C₁-C₆ alkoxycarbonyl.

Particularly preferred compounds within this group are those in which R⁵ represents phenyl optionally substituted with one or two substituents independently selected from —NHC(O)R¹², —NHC(O)NR¹⁶R¹⁷, hydroxyl or C₁-C₆ alkoxy, or in which R⁵ represents phenyl optionally substituted with one, two or three substituents independently selected from halogen, hydroxyl, or carboxyl, or in which R⁵ is a bicyclic unsaturated ring system containing 10 ring atoms, the ring system being substituted with one or two ring heteroatoms independently selected from nitrogen and oxygen, the ring system being optionally substituted with oxo.

It will be appreciated that the number and nature of substituents on rings in the compounds of the invention will be selected so as to avoid sterically undesirable combinations Examples of preferred compounds of the invention include:

N-(2-{[(2S)-2-amino-3-(5-chloro-1'H,3H-spiro[1-benzofuran-2,4'-piperidin]-1'-yl)propyl]oxy}-4-methoxyphenyl)acetamide;

N-(2-{[(2S)-2-amino-3-(5-chloro-1'H,3H-spiro[1-benzofuran-2,4'-piperidin]-1'-yl)propyl]oxy}-4-hydroxyphenyl)acetamide bis(trifluoroacetate) (salt);

N-(2-{[(2S)-2-amino-3-(5-fluoro-1'H,3H-spiro[1-benzofuran-2,4'-piperidin]-1'-yl)propyl]oxy}-4-methoxyphenyl)acetamide;

N-(2-{[(2S)-2-amino-3-(5-fluoro-1'H,3H-spiro[1-benzofuran-2,4'-piperidin]-1'-yl)propyl]oxy}-4-hydroxyphenyl)acetamide bis(trifluoroacetate) (salt);

N-(2-{[(2S)-2-Amino-3-(1'H,3H-spiro[1-benzofuran-2,4'-piperidin]-1'-yl)propyl]oxy}-4-methoxyphenyl)acetamide;

N-(2-{[(2S)-2-Amino-3-(1'H,3H-spiro[1-benzofuran-2,4'-piperidin]-1'-yl)propyl]oxy}-4-hydroxyphenyl)acetamide bis(trifluoroacetate) (salt);

N-(2-{[(2S)-2-(Acetylamino)-3-(5-fluoro-1'H,3H-spiro[1-benzofuran-2,4'-piperidin]-1'-yl)propyl]oxy}-4-methoxyphenyl)acetamide;

N-{2-[3-Amino-2-(5-chloro-1'H,3H-spiro[1-benzofuran-2,4'-piperidin]-1'-yl)propoxy]-4-methoxyphenyl}acetamide bis(trifluoroacetate);

N-{2-[3-Amino-2-(5-fluoro-1'H,3H-spiro[1-benzofuran-2,4'-piperidin]-1'-yl)propoxy]-4-methoxyphenyl}acetamide bis(trifluoroacetate);

N-{2-[3-Amino-2-(1'H,3H-spiro[1-benzofuran-2,4'-piperidin]-1'-yl)propoxy]-4-methoxyphenyl}acetamide bis(trifluoroacetate);

N-{2-[3-Amino-2-(5-chloro-1'H,3H-spiro[1-benzofuran-2,4'-piperidin]-1'-yl)propoxy]phenyl}urea bis(trifluoroacetate);

N-{2-[3-Amino-2-(5-fluoro-1'H,3H-spiro[1-benzofuran-2,4'-piperidin]-1'-yl)propoxy]phenyl}urea bis(trifluoroacetate);

N-{2-[2-Chloro-3-(5-chloro-1'H,3H-spiro[1-benzofuran-2,4'-piperidin]-1'-yl)propoxy]-4-hydroxyphenyl}acetamide trifluoroacetate (salt);

N-{2-[2-(5-Chloro-1'H,3H-spiro[1-benzofuran-2,4'-piperidin]-1'-yl)propoxy]-4-methoxyphenyl}acetamide trifluoroacetate;

5-{[(2S)-2-Amino-3-(5-fluoro-1'H,3H-spiro[1-benzofuran-2,4'-piperidin]-1'-yl)propyl]oxy}-2H-1,4-benzoxazin-3(4H)-one;

8-{[(2S)-2-Amino-3-(5-fluoro-1'H,3H-spiro[1-benzofuran-2,4'-piperidin]-1'-yl)propyl]oxy}quinolin-2(1H)-one;

5-Chloro-2-[2-chloro-3-(5-chloro-1'H,3H-spiro[1-benzofuran-2,4'-piperidin]-1'-yl)propoxy]-4hydroxybenzoic acid;

2-[2-Amino-3-(5-chloro-1'H,3H-spiro[1-benzofuran-2,4'-piperidin]-1'-yl)propoxy]-5-chloro-4hydroxybenzoic acid;

5-chloro-2-[3-(5-chloro-1'H,3H-spiro[1-benzofuran-2,4'-piperidin]-1'-yl)-2-(methylamino)propoxy]-4-hydroxybenzoic acid;

5-chloro-2-[3-(5-chloro-1'H,3H-spiro[1-benzofuran-2,4'-piperidin]-1'-yl)-2-(dimethylamino)propoxy]-4hydroxybenzoic acid and pharmaceutically acceptable salts and solvates of any one thereof.

The present invention further provides a process for the preparation of a compound of formula (I)

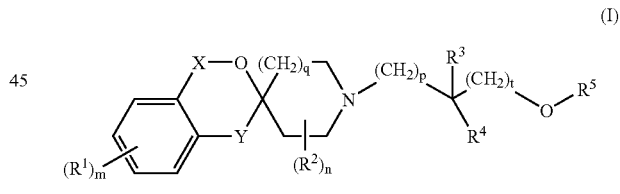

(I)

or a pharmaceutically acceptable salt or solvate thereof as defined above which comprises, (a) converting a compound of formula (II)

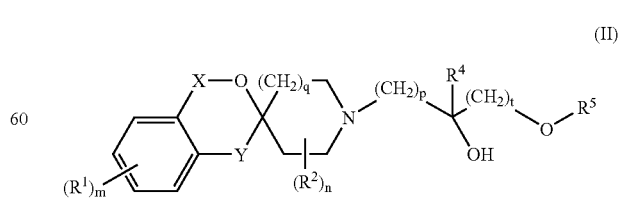

(II)

wherein R¹, m, X, Y, R², n, q, p, R⁴, t and R⁵ are as defined in formula (I), into a compound of formula (I); or (b) reacting a compound of formula (III)

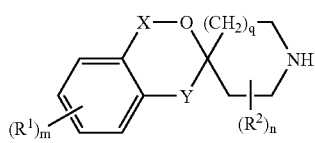

(III)

wherein $R^1$, m, X, Y, $R^2$, n and q are as defined for formula (I), with a compound of formula (IV)

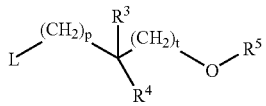

(IV)

wherein L is a leaving group (for example a hydroxyl group or a methylsulphonyloxy group) and p, $R^3$, $R^4$, t and $R^5$ are as defined for formula (I);

(c) reacting a compound of formula (V)

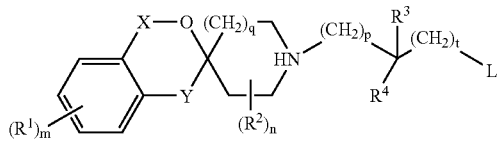

(V)

wherein $R^1$, m, X, Y, $R^2$, n, q, p, , $R^3$, $R^4$ and t are as defined for formula (I), with a compound of formula (VI)

 (VI)

wherein L is a leaving group (for example a methylsulphonyloxy group or nitrobenzenesulfonyloxy group) and $R^5$ is as defined for formula (I);

and optionally thereafter if necessary:
(i) converting a compound of formula (I) into another compound of formula (I);
(ii) removing any protecting groups; or
(iii) forming a pharmaceutically acceptable salt or solvate.

The processes of the invention may conveniently be carried out in a solvent, e.g. an organic solvent such as an alcohol (e.g. methanol or ethanol), a hydrocarbon (e.g. toluene) or tetrahydrofuran, dimethylformamide, N-methylpyrrolidinone, dichloromethane or acetonitrile at a temperature of, for example, 0° C. or above such as a temperature in the range from 0, 5, 10, 15 or 20° C. to 100, 110 or 120° C.

Conversion of a compound of formula (II) into a compound of formula (I) according to process (a) involves substituting the desired $R^3$ substituent for the hydroxyl group shown in the formula. This may be performed using processes known in the art such as are illustrated in the examples. An amino group, for example, may be introduced by reacting the corresponding hydroxy derivative with di-tert-butyl imidocarbonate in the presence of suitable coupling reagents such as triphenylphosphine and diethyl azodicarboxylate, and a suitable solvent such as tetrahydrofuran.

Compounds of formulae (II), (III), and (IV), (V) and (VI) are either commercially available, are known in the literature or may be prepared using known techniques. Examples of preparation methods for certain of these compounds are given hereinafter in is the examples.

Compounds of formula (II), where p is 1, may be prepared, for example, by reacting a compound of formula (VII)

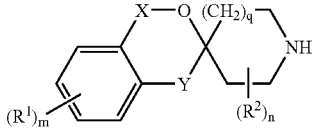

(VII)

wherein $R^1$, m, X, Y, $R^2$, n and q are as defined in formula (I), with a compound of formula (VII)

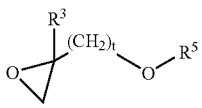

(VIII)

wherein $R^3$ and $R^5$ are as defined in formula (I), and t is 1 or 2

Compounds of formula (VII) and (VIII) are themselves either commercially available, are known in the literature or may be prepared using known techniques.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) have activity as pharmaceuticals, in particular as modulators of chemokine receptor (especially MIP-1α chemokine receptor) activity, and may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:
(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease;

(7) cancers, especially non-small cell lung cancer (NSCLC) and squamous sarcoma;

(8) diseases in which angiogenesis is associated with raised chemokine levels; and (9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease (e.g. rheumatoid arthritis) which comprises administering to a patient in need thereof a therapeutically effective amount of a compound of formula (I), or a pharmaceutically acceptable salt or solvate thereof, as hereinbefore defined.

The invention still further provides a method of treating an airways disease (e.g. asthma or chronic obstructive pulmonary disease) which comprises administering to a patient in need thereof a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The invention will now be further illustrated by the following non-limiting examples.

$^1$H NMR spectra were recorded on Varian Unity Inova 400. The central solvent peak of chloroform-d ($\delta_H$ 7.27 ppm), acetone-d$_6$ ($\delta_H$ 2.05 ppm), DMSO-d$_6$ ($\delta_H$ 2.50 ppm), or methanol-d$_4$ ($\delta_H$ 4.87 ppm) were used as internal standard.

Low resolution mass spectra and accurate mass determination were recorded on a Hewlett-Packard 1100 LC-MS system equipped with APCI/ESI ionisation chambers.

All solvents and commercial reagents were laboratory grade and used as received.

The nomenclature used for the compounds was generated with ACD/Name and ACD/Name Batch.

The abbreviations or terms used in the examples have the following meanings:
DEAD: diethyl azodicarboxylate
DMF: N,N-dimethylformamide
DMSO: dimethyl sulfoxide
THF: tetrahydrofuran
TMSCl: chlorotrimethylsilane

EXAMPLES

Intermediate compound: 5-Chloro-3H-spiro[1-benzofuran-2,4'-piperidine]

Method A: This compound was prepared as described by Effland, R. R; Gardner, B. A; Strupczewski, J. *J. Heterocyclic Chem.* 1981, 18, 811-814.

Method B:

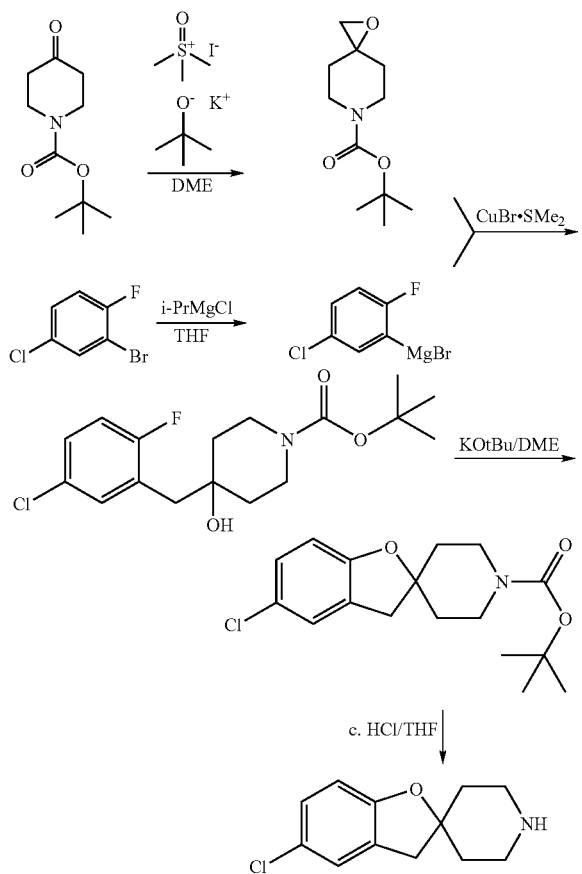

Step I tert-Butyl 1-oxa-6-azaspiro[2.5]octane-6-carboxylate

Potassium tert.-butoxide (31 g) was added to a stirred suspension of trimethylsulfoxonium iodide (60.8 g) in 1,2-dimethoxyethane (250 mL) at 20° C. After 1 hour, the mixture was added portionwise over 30 minutes to a stirred solution of 4-oxo-1-piperidinecarboxylic acid, 1,1-dimethylethyl ester (50 g) in 1,2-dimethoxyethane (50 mL) at 0° C. After a further 2 hours, water (500 mL) was added and the mixture was extracted with tert.-butyl methyl ether (2×500 mL). The organic extracts were washed separately with saturated sodium bicarbonate solution (250 mL). The combined organic layer was dried over anhydrous magnesium sulfate, filtered and evaporated under reduced pressure. The residual oil was co-evaporated with toluene (100 mL) to give the sub-title compound (43.25g) as a solid. $^1$H-NMR (CDCl$_3$, 400 MHz): δ 3.75-3.70 (m, 2H); 3.47-3.38 (m, 2H); 2.69 (s, 2H); 1.84-1.75 (m, 2H); 1.48-1.43 (m, 2H); 1.46 (s, 9H).

Step II tert-Butyl 5-chloro-1'H,3H-spiro[1-benzofuran-2,4'-piperidine]-1'-carboxylate A solution of iso-propylmagnesium chloride in tetrahydrofuran (THF) (2M, 106 mL) was added dropwise over 15 minutes to a stirred solution of 2-bromo-4-chloro-1-fluorobenzene (42.5 g) in anhydrous tetrahydrofuran (250 mL) at 0° C. under nitrogen. After a further 15 minutes, a solution of tert-butyl 1-oxa-6-azaspiro[2.5]octane-6-carboxylate (43.2 g) in anhydrous tetrahydrofuran (50 mL) was added followed by copper (I) bromide dimethyl sulphide complex (0.4 g). The mixture was stirred at 40° C. for 18 hours, cooled to 20° C., diluted with water (300 mL) and extracted with tert.-butyl methyl ether (2×300 mL). Organic extracts were dried over anhydrous magnesium sulphate, filtered and evaporated under reduced pressure. The residual oil was dissolved in 1,2-dimethoxypropane (200 mL). Potassium tert.-butoxide (22.8 g) was added and the mixture stirred at 40° C. for 16 hours then at 50° C. for 24 hours. Further potassium tert.-butoxide (5.7 g) was added and stirring continued at 50° C. for 2 hours then at 55° C. for 4 hours. Water (500 mL) was added and the mixture extracted with tert.-butyl methyl ether (2×300 mL). Organic extracts were dried over anhydrous magnesium sulphate, filtered and evaporated under reduced pressure to give the sub title compound (47.45 g) as an oil. $^1$H-NMR (CDCl$_3$, 400 MHz): δ 7.10 (s, 1H); 7.06 (d, 1H); 6.67 (d, 1H); 3.80-3.65 (m, 2H); 3.39 (dt, 2H); 2.94 (s, 2H); 1.93-1.85 (m, 2H); 1.67 (dt, 2H); 1.47 (s, 9H).

Step III

5-Chloro-3H-spiro[1-benzofuran-2,4'-piperidine]

Concentrated hydrochloric acid (23 mL) was added to a solution of tert-butyl 5-chloro-1'H,3H-spiro[1-benzofuran-2,4'-piperidine]-1'-carboxylate (46.43 g) in tetrahydrofuran (230 mL). The mixture was stirred at 50° C. for 6 hours, cooled to 20° C., diluted with water (230 mL) and extracted with tert.-butyl methyl ether (2×230 mL). The aqueous phase was adjusted to pH>10 by addition of 50 wt. % sodium hydroxide solution and extracted with tert.-butyl methyl ether (3×300 mL). Organic extracts were dried over anhydrous magnesium sulphate, filtered and evaporated under reduced pressure. The residual oil was dissolved in tetrahydrofuran (240 mL), concentrated hydrochloric acid (12 mL) was added and the mixture stirred at 20° C. for 16 hours. Precipitated solid was filtered and dissolved in water (100 mL). The solution was adjusted to pH>10 by addition of 50 wt. % sodium hydroxide solution and extracted with tert.-butyl methyl ether (3×100 mL) to give the title compound (13.3 g) as a solid. $^1$H-NMR (CDCl$_3$, 400 MHz):δ 7.13 (s, 1H); 7.04 (d, 1H); 6.65 (d, 1H); 3.03-2.98 (m, 4H); 2.84-2.78 (m, 2H); 1.87-1.83 (m, 2H); 1.76-1.69 (m, 2H). APCI-MS: m/z 224(MH$^+$).

Intermediate compound: 5-Fluoro-3H-spiro[1-benzofuran-2,4'-piperidine]

Method A:

Step I

1'-Benzyl-5-fluoro-3H-spiro[1-benzofuran-2,4'-piperidine]

To a suspension of magnesium strip (763 mg) in diethyl ether (7 mL) was added iodine (one crystal) followed by 0.4 mL of 2-(bromomethyl)-1,4-difluorobenzene under nitrogen. The reaction was initiated with a heat gun and 2-(bromomethyl)-1,4-difluorobenzene (5.0 g, 24.25 mmol) in diethyl ether (7 mL) was added slowly. After addition was completed the reaction mixture was refluxed for 100 minutes, cooled to room temperature. To this is reaction mixture a solution of 1-benzylpiperidin-4-one (4.57 g, 24.24 mmol) in diethyl ether (12 mL) was added dropwise with vigorous stirring. After addition was completed the mixture was left at room temperature over night. Saturated aqueous NH$_4$Cl solution (excess) was added and stirred at room temperature until hydrolysis was completed and the mixture was extracted with diethyl ether. The organic layer was washed with H₂O, dried over Na₂SO₄, filtered and concentrated in vacuo. The residue was purified by silica gel flash chromatography (0-1% methanol in dichloromethane, 0.2% NH₄OH) to give intermediate 1-benzyl-4-(2,5-difluorobenzyl)piperidin-4-ol (2.74 g) containg large quantities of unknown impurities. To a suspension of NaH (55%, 1.12 g, 26.0 mmol) in toluene (10 mL) was added slowly a solution of 1-benzyl-4-(2,5-difluorobenzyl) piperidin-4-ol in toluene (15 mL). After addition was completed the reaction mixture was stirred at 110° C. (in a pre heated oil bath), after 5 minutes, DMF (9 mL) was added and the mixture was refluxed for 2 hours. The reaction mixture was cooled to room temperature, water (20 mL) was added and extracted with ethyl acetate. The organic layer was dried over Na₂SO₄, filtered and concentrated in vacuo. The residue was purified by silica gel flash chromatography (0-1.5% methanol in dichloromethane, 0.2% NH₄OH) to give sub title compound (190 mg). ¹H-NMR (CDCl₃, 400 MHz): δ 7.39-7.26 (m, 5H); 6.88-6.76 (m, 2H); 6.67 (dd, J=4.2, 8.7 Hz, 1H); 3.59 (s, 2H); 2.99 (s, 2H); 2.68-2.47 (m, 4H); 2.03-1.94 (m, 2H); 1.86-1.76 (m, 2H).

APCI-MS: m/z 298(MH⁺).

Step I 5-Fluoro-3H-spiro[1-benzofuran-2,4'-piperidine]

Ethyl chloroformate (65.6 mg, 0.604 mmol) was added to a solution of 1'-benzyl-5-fluoro-3H-spiro[1-benzofuran-2,4'-piperidine] (150 mg, 0.504 mmol) in toluene (2 mL) and the mixture was refluxed over night, cooled to room temperature, diluted by addition of toluene (10 mL), washed successively with saturated aqueous NaHCO₃ solution and water. The organic layer was dried over Na₂SO₄, filtered and concentrated in vacuo. The residue was dissolved in ethanol (3.5 mL), aqueous KOH (800 mg, KOH in 0.8 mL H₂O) was added and the mixture was refluxed over night, cooled to room temperature, ethanol was removed in vacuo. Aqueous layer was extracted with diethyl ether. Combined ether layer is was washed with 3N aqueous HCl. Aqueous layer was adjusted to pH 10 by addition of aqueous 3N NaOH. The basic solution was extracted with ethyl acetate. Combined organic layer was washed with water, dried over Na₂SO₄, filtered and concentrated in vacuo. The residue was purified by HPLC (10-55% CH₃CN in H₂O, 0.1% NH₄OH) to give the title compound (49 mg). ¹H-NMR (CD₃OD, 400 MHz): δ 6.92-6.87 (m, 1H); 6.81-6.75 (m, 1H); 6.64 (dd, J=4.2, 8.7 Hz, 1H); 3.08-2.98 (m, 4H); 2.89-2.81 (m, 2H); 1.91-1.83 (m, 2H); 1.78-1.69 (m, 2H).

APCI-MS: m/z 208(MH⁺).

Method B:

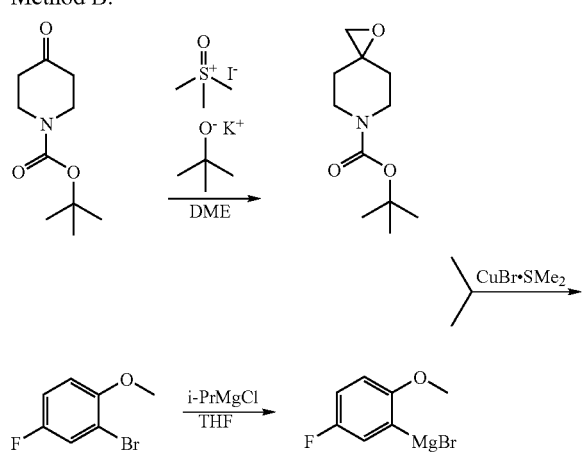

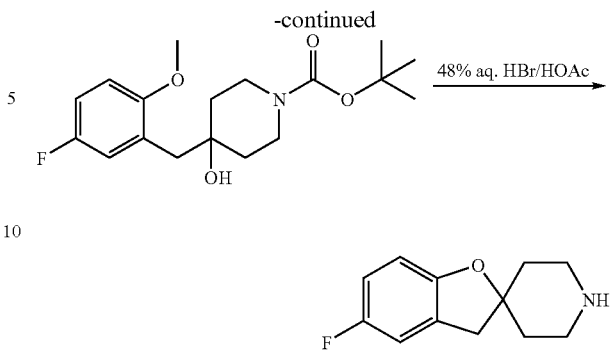

Step I tert-Butyl 4-(5-fluoro-2-methoxybenzyl)-4-hydroxypiperidine-1-carboxylate A solution of iso-propylmagnesium chloride in tetrahydrofuran (2M, 130 mL) was added dropwise over 30 minutes to a stirred solution of 2-bromo-4-fluoroanisole (34.2 mL) in anhydrous tetrahydrofuran (400 mL) at 30° C. under nitrogen. After a further 16 hours at 30° C., copper (I) bromide dimethyl sulphide complex (0.4 g) was added followed by solution of tert-butyl 1-oxa-6-azaspiro[2.5]octane-6-carboxylate (56.2 g) in anhydrous tetrahydrofuran (110 mL). After a further 3 hours at 30° C., the solution was cooled to 20° C., diluted with water (600 mL) and extracted with tert.-butyl methyl ether (600 mL) then ethyl acetate (600 mL). Combined organic extracts were dried over anhydrous magnesium sulphate, filtered and evaporated under reduced pressure to give crude sub-title compound (86 g) as a solid.

APCI-MS: m/z 240 [M+H—(CH₃)₂CCH₂—CO₂]⁺

Step II

5-Fluoro-3H-spiro[1-benzofuran-2,4'-piperidine]

Hydrobromic acid (48%, 60 mL) was added to a solution of the crude tert-butyl 4-(5-fluoro-2-methoxybenzyl)-4-hydroxypiperidine-l-carboxylate (86 g) in acetic acid (300 mL). The mixture was heated at reflux for 5 hours. Further hydrobromic acid (48%, 60 mL) was added and reflux continued for 24 hours. The mixture was cooled to room temperature, added to water (2 L) and extracted with tert.-butyl methyl ether (2×500 mL). The aqueous phase was adjusted to pH>10 by addition of 50 wt. % sodium hydroxide solution and extracted with tert.-butyl methyl ether (2L+1L). Organic extracts were dried over anhydrous magnesium sulphate, filtered and evaporated under reduced pressure. The residual solid was crystallised from tetrahydrofuran/tert.-butyl methyl ether (4:1, 500 mL) to give the title compound (20 g). ¹H-NMR (CD₃OD, 400 MHz): δ 6.92-6.87 (m, 1H); 6.81-6.75 (m, 1H); 6.64 (dd, J=4.2, 8.7 Hz, 1H); 3.08-2.98 (m, 4H); 2.89-2.81 (m, 2H); 1.91-1.83 (m, 2H); 1.78-1.69 (m, 2H).

APCI-MS: m/z 208(MH⁺).

Example 1

N-(2-{[(2S)-2-amino-3-(5-chloro-1'H,3H-spiro[1-benzofuran-2,4'-piperidin]-1'-yl)propyl]oxy}-4-methoxyphenyl)acetamide Step I

(2R)-2-[(5-Methoxy-2-nitrophenoxy)methyl]oxirane

To a stirred solution of 5-methoxy-2-nitrophenol (2.11 g, 12.5 mmol) and 2(S)-oxyran-2-ylmethanol (0.926 g, 12.5 mmol) in $CH_2Cl_2$ (150 mL) was added polymer bound triphenylphosphine (6.2 g, 18.7 mmol). The mixture was stirred at room temperature for 15 minutes, then cooled to 0° C., DEAD (3.65 g, 18.7 mmol) was added dropwise. After addition was completed the reaction mixture was stirred at 0° C. for 2 hours. Then ice-bath was removed and the reaction mixture was stirred at room temperature over the week end. The polymer bound reagent was removed by filtration through celite. The filtrate was concentrated in vacuo, tert.-butyl methyl ether (100 mL) was added and stirred at room temperature for 30 minutes to obtain a precipitation and clear solution. The precipitate was filtered off and washed with tert-butyl methyl ether. The filtrate was concentrated in vacuo the residue was purified by silica gel flash chromatography (heptane/ethyl acetate) to give the sub-title compound (1.45 g).

$^1$H-NMR ($CDCl_3$, 400 MHz): δ 8.00 (d, J=9.1 Hz, 1H); 6.60 (d, J=2.5 Hz, 1H); 6.55 (dd, J=2.5, 9.1 Hz, 1H); 4.42 (dd, J=2.7, 11.2 Hz, 1H); 4.13 (dd, J=5.1, 11.2 Hz, 1H); 3.88 (s, 3H); 3.41 (m, 1H); 2.92 (m, 2H).

Step II

(2R)-1-(5-chloro-1'H,3H-spiro[1-benzofuran-2,4'-piperidin]-1'-yl)-3-(5-methoxy-2-nitrophenoxy)propan-2-ol A mixture of 5-chloro-3H-spiro[1-benzofuran-2,4'-piperidine] (396 mg, 1.77 mmol) and (2R)-2-[(5-methoxy-2-nitrophenoxy)methyl]oxirane (400 mg, 1.77 mmol) in ethanol (5 mL) was stirred at 88° C. for 4 hours. The volatiles were removed in vacuo and the residue was purified by silica gel flash chromatography (0-2% methanol in dichloromethane, 0.2% $NH_4OH$) to give the sub-title compound (700 mg).

$^1$H-NMR ($CDCl_3$, 400 MHz): δ 8.02 (d, J=9.1 Hz, 1H); 7.12 (s, 1H); 7.07 (dd, J=2.2, 8.5 Hz, 1H); 6.68 (d, J=8.5 Hz, 1H); 6.58 (d, J=2.5 Hz, 1H); 6.55 (dd, J=2.5, 9.1 Hz, 1H); 4.26-4.12 (m, 3H); 3.90 (s, 3H); 3.00 (s, 2H); 2.98-2.65 (m, 6H); 2.06-1.82 (m, 4H).

APCI-MS: m/z 449(MH$^+$).

Step III

N-(2-{[(2R)-3-(5-chloro-1'H,3H-spiro[1-benzofuran-2,4'-piperidin]-1'-yl)-2-hydroxypropyl]oxy}-4-methoxyphenyl)acetamide (2R)-1-(5-chloro-1'H,3H-spiro[1-benzofuran-2,4'-piperidin]-1'-yl)-3-(5-methoxy-2-nitrophenoxy)propan-2-ol (700 mg, 1.56 mmol) was dissolved in ethyl acetate (35 mL), Pt/C (5%, 121 mg) was added and hydrogeneted at room temperature at atmospheric pressure for 3 hours. After hydrogenation was completed, acetic anhydride (0.22 mL, 2.34 mmol) was added and the reaction mixture was stirred at room temperature for 1 hour. The catalyst was filtered off, the filtrate was concentrated in vacuo and the residue was dissolved in methanol (10 mL), 2 drops of concentrated aqueous NaOH was added and the mixture was refluxed for 3 hours, cooled to room temperature. The pH of the reaction mixture was adjusted to 2 by addition of aqueous hydrochloric acid, concentrated and the residue was purified by silica gel flash chromatography (0-4% methanol in dichloromethane, 0.2% $NH_4OH$) to give the sub-title compound (620 mg).

$^1$H-NMR ($CDCl_3$, 400 MHz): δ 8.18 (d, J=8.8 Hz, 1H); 8.10 (br.s, 1H); 7.12 (s, 1H); 7.08 (dd, J=2.2, 8.4 Hz, 1H); 6.68 (d, J=8.4 Hz, 1H); 6.57-6.50 (m, 2H); 4.18 (m, 1H); 4.06 (dd, J=3.3, 10.2 Hz, 1H); 3.96 (dd, J=5.5, 10.2 Hz, 1H); 3.79 (s, 3H); 3.02 (s, 2H); 2.96 (m, 2H); 2.82-2.58 (m, 4H); 2.22 (s, 3H); 2.00 (m, 4H).

APCI-MS: m/z 461(MH$^+$).

Step IV

N-(2-{[(2S)-2-amino-3-(5-chloro-1'H,3H-spiro[1-benzofuran-2,4'-piperidin]-1'-yl)propyl]oxy}-4-methoxyphenyl)acetamide To a mixture of N-(2-{[(2R)-3-(5-chloro-1'H,3H-spiro[1-benzofuran-2,4'-piperidin]-1'-yl)-2-hydroxypropyl]oxy}-4-methoxyphenyl)acetamide (610 mg, 1.32 mmol), triphenylphosphine (692 mg, 2.64 mmol) and di-tert-butyl imidodicarbonate (574 mg, 2.64 mmol) in THF (6 mL) was added DEAD (460 mg, 2.64 mmol) in THF (4 mL) dropwise at 0° C. After addition was completed, the reaction mixture was stirred at room temperature over night. The volatiles were removed in vacuo and the residue was treated with aqueous trifluoroacetic acid (0.4 mL of $H_2O$ in 7.6 mL of $CF_3CO_2H$) at room temperature for 15 minutes. The volatiles were removed in vacuo and the residue was purified by silica gel flash chromatography (0-3% methanol in dichloromethane, 0.2% $NH_4OH$) to give the title compound (81 mg).

$^1$H-NMR ($CD_3OD$, 400 MHz): δ 7.66 (d, J=8.8 Hz, 1H); 7.13 (m, 1H); 7.04 (dd, J=2.2, 8.5 Hz, 1H); 6.65 (d, J=8.5 Hz, 1H); 6.59 (d, J=2.6 Hz, 1H); 6.49 (dd, J=2.6, 8.8 Hz, 1H); 4.10 (dd, J=3.3, 9.6 Hz, 1H); 3.90 (dd, J=6.5, 9.6 Hz, 1H); 3.78 (s, 3H); 3.38 (m, 1H); 3.02 (s, 2H); 2.75-2.46 8m, 6H); 2.16 (s, 3H); 1.98-1.77 (m, 4H).

APCI-MS: m/z 460(MH$^+$).

It also yielded N-{2-[3-Amino-2-(5-chloro-1'H,3H-spiro[1-benzofuran-2,4'-piperidin]-1'-yl)propoxy]-4-methoxyphenyl}acetamide (84 mg) as a byproduct, see Example 8.

Example 2

N-(2-{[(2S)-2-amino-3-(5-chloro-1'H,3H-spiro[1-benzofuran-2,4'-piperidin]-1'-yl)propyl]oxy}-4-methoxyphenyl)acetamide To a cold (ice-water) solution of N-(2-{[(2S)-2-amino-3-(5-chloro-1'H,3H-spiro[1-benzofuran-2,4'-piperidin]-1'-yl)propyl]oxy}-4-methoxyphenyl)acetamide (65 mg, 0.141 mmol) in $CH_2Cl_2$ (3 mL) was added slowly a solution of $BBr_3$ in $CH_2Cl_2$ (1 M, 0.42 mL, 0.42 mmol) under nitrogen atmosphere. After the addition was completed, the reaction mixture was stirred at 0° C. for 3.5 hours, additional 1(M) solution of $BBr_3$ in $CH_2Cl_2$ (0.2 mL) was added and the mixture was stirred at the same temperature for an additional hour, methanol (2 mL) was added slowly and stirring was continued at 0° C. for 20 minutes. The volatiles were removed in vacuo and the residue was dissolved in methanol (5 mL), concentrated aqueous $NH_4OH$ (1 mL) was added and after 5 minutes the volatiles were removed in vacuo and the residue was purified by HPLC (10-65% acetonitrile in water, 0.1% $CF_3CO_2H$) to give the title compound (31 mg).

$^1$H-NMR ($CD_3OD$, 400 MHz): δ 7.27 (d, J=8.6 Hz, 1H); 7.18 (m, 1H); 7.08 (dd, J=2.2, 8.6 Hz, 1H); 6.70 (d, J=8.6 Hz, 1H); 6.54 (d, J=2.4 Hz, 1H); 6.45 (dd, J=2.4, 8.6 Hz, 1H); 4.35 (dd, J=3.3, 10.9 Hz, 1H); 4.19 (dd, J=5.9, 10.9 Hz, 1H); 4.04 (br.s, 1H); 3.28-2.98 (m, 8H); 2.15 (s, 3H); 2.16-2.01 (m, 4H).

APCI-MS: m/z 446(MH$^+$).

Example 3

N-(2-{[(2S)-2-amino-3-(5-fluoro-1'H,3H-spiro[1-benzofuran-2,4'-piperidin]-1'-yl)propyl]oxy}-4-methoxyphenyl)acetamide Step I (2R)-2-[(5-Methoxy-2-nitrophenoxy)methyl]oxirane To a mixture of (2S)-oxiran-2-ylmethanol (445 mg, 6.0 mmol), 5-methoxy-2-nitrophenol (1.02 g, 6.0 mmol) and triphenylphosphine (1.57 g, 6.0 mmol) in THF (10 mL) was added DEAD (0.95 mL, 6.0 mmol) in THF (5 mL) dropwise at 0° C. After addition was completed the ice bath was removed and the mixture was stirred at room temperature over night. The volatiles were removed in vacuo and the residue was purified by silica gel flash chromatography (0-40% ethyl acetate in petroleum spirit) to give the sub-title compound (820 mg).

$^1$H-NMR ($CDCl_3$, 400 MHz): δ 8.00 (d, J=9.1 Hz, 1H); 6.60 (d, J=2.5 Hz, 1H); 6.54 (dd, J=2.5, 9.1 Hz, 1H); 4.41 (dd, J=2.7, 11.3 Hz, 1H); 4.12 (dd, J=5.0, 11.3 Hz, 1H); 3.88 (s, 3H); 3.41 (m, 1H); 2.92 (m, 2H).

APCI-MS: m/z 226(MH$^+$).

Step II

N-{4-methoxy-2-[(2R)-oxiran-2-ylmethoxy]phenyl}acetamide

A mixture of (2R)-2-[(5-methoxy-2-nitrophenoxy)methyl]oxirane (620 mg, 2.75 mmol), Pd/C (10%, 250 mg), N-ethyl-N-isopropylpropan-2-amine (0.94 mL, 5.5 mmol) and acetic anhydride (0.52 mL, 5.5 mmol) in ethyl acetate (25 mL) was hydrogenated at atmospheric pressure at room temperature for 40 minutes. The catalyst was filtered off and the filtrate was concentrated in vacuo. The residue was purified by silica gel flash chromatography (0-60% ethyl acetate in petroleum spirit) to give sub-title compound (155 mg) and 204 mg of N-[2-(2-hydroxypropoxy)-4-methoxyphenyl]acetamide (see example 14). $^1$H-NMR ($CDCl_3$, 400 MHz): δ 8.22 (d, J=8.8 Hz, 1H); 7.64 (br.s, 1H); 6.55-6.49 (m, 2H); 4.34 (dd, J=2.5, 11.3 Hz, 1H); 3.94 (dd, J=6.1, 11.3 Hz, 1H); 3.78 (s, 3H); 3.39 (m, 1H); 2.96 (t, J=4.5 Hz, 1H); 2.78 (dd; J=2.6, 4.8 Hz, 1H); 2.20 (s, 3H).

APCI-MS: m/z 238(MH$^+$).

Step III

N-(2-{[(2R)-3-(5-fluoro-1'H,3H-spiro [1-benzofuran-2,4'-piperidin]-1'-yl)-2-hydroxypropyl]oxy}-4-methoxyphenyl)acetamide A mixture of 5-fluoro-3H-spiro[1-benzofuran-2,4'-piperidine] (250 mg, 1.02 mmol) and N-{4-methoxy-2-[(2R)-oxiran-2-ylmethoxy]phenyl}acetamide (150 mg, 0.632 mmol) in ethanol (3 mL) was stirred at 80° C. over night. The volatiles were removed in vacuo and the residue was purified by silica gel flash chromatography (0-1.5% methanol in dichloromethane, 0.2% $NH_4OH$) to give the sub-title compound (266 mg).

$^1$H-NMR ($CD_3OD$, 400 MHz): δ 7.74 (d, J=8.8 Hz, 1H); 6.90 (dd, J=2.6, 8.2 Hz, 1H); 6.77 (m, 1H); 6.65-6.60 (m, 2H); 6.51 (dd, J=2.6, 8.8 Hz, 1H); 4.17 (m, 1H); 4.09 (dd, J=3.4, 9.9 Hz, 1H); 3.96 (dd, J=6.2, 9.9 Hz, 1H); 3.78 (s, 3H); 3.01 (s, 2H); 2.70 (br.s, 4H); 2.61 (m, 2H); 2.15 (s, 3H); 1.97-1.81 (m, 4H).

APCI-MS: m/z 445(MH$^+$).

Step IV

N-(2-{[(2S)-2-amino-3-(5-fluoro-1'H,3H-spiro[1-benzofuran-2,4'-piperidin]-1'-yl)propyl]oxy}-4-methoxyphenyl)acetamide To a mixture of N-(2-{[(2R)-3-(5-fluoro-1'H,3H-spiro[1-benzofuran-2,4'-piperidin]-1'-yl)-2-hydroxypropyl]oxy}-4-methoxyphenyl)acetamide (260 mg, 0.58 mmol), triphenylphosphine (228 mg, 0.87 mmol) and di-tert-butyl imidodicarbonate (189 mg, 0.87 mmol) in THF (3 mL) was added DEAD (0.137 mL, 0.87 mmol) in THF (1.5 mL) dropwise at 0° C. After addition was completed, the reaction mixture was stirred at room temperature over night. The volatiles were removed in vacuo and the residue was treated with aqueous trifluoroacetic acid (0.2 mL of $H_2O$ in 3.8 mL of $CF_3CO_2H$) at room temperature for 30 minutes. The volatiles were removed in vacuo and the residue was purified by silica gel flash chromatography (0-2% methanol in dichloromethane, 0.2% $NH_4OH$) to give the title compound (45 mg).).

$^1$H-NMR ($CD_3OD$, 400 MHz): δ 7.65 (d, J=8.8 Hz, 1H); 6.89 (dd, J=2.7, 8.1 Hz, 1H); 5 6.77 (m, 1H); 6.62 (dd, J=4.2, 8.7 Hz, 1H); 6.60 (d, J=2.6 Hz, 1H); 6.50 (dd, J=2.6, 8.8 Hz, 1H); 4.10 (dd, J=3.3, 9.7 Hz, 1H); 3.90 (dd, J=6.6, 9.7 Hz, 1H); 3.79 (s, 3H); 3.38 (m, 1H); 3.01 (s, 2H); 2.76-2.46 (m, 6H); 2.15 (s, 3H); 1.94 (m, 2H); 1.82 (m, 2H).

APCI-MS: m/z 444(MH$^+$).

From this reaction mixture, N-{2-[3-amino-2-(5-chloro-1'H,3H-spiro[1-benzofuran-2,4'-piperidin]-1'-yl)propoxy]-4-methoxyphenyl}acetamide (22 mg) was obtained as byproduct, (see example 9)

Example 4

N-(2-{[(2S)-2-amino-3-(5-fluoro-1'H,3H-spiro[1-benzofuran-2,4'-piperidin]-1'-yl)propyl]oxy}-4-hydroxyphenyl)acetamide bis(trifluoroacetate) (salt)

To a cold (ice-water) solution of N-(2-{[(2S)-2-amino-3-(5-fluoro-1'H,3H-spiro[1-benzofuran-2,4'-piperidin]-1'-yl)propyl]oxy}-4-methoxyphenyl)acetamide (43 mg, 0.097 mmol) in $CH_2Cl_2$ (2 mL) was added a solution of $BBr_3$ in $CH_2Cl_2$ (1 M, 0.29 mL, 0.29 mmol) slowly under nitrogen atmosphere. After the addition was completed, the reaction mixture was stirred at 0° C. for 3 hours, methanol (1 mL) was added slowly and stirring was continued at 0° C. for 30 minutes. The volatiles were removed in vacuo and the residue was dissolved in methanol (5 mL), concentrated aqueous $NH_4OH$ (1 mL) was added and after 5 minutes the volatiles were removed in vacuo and the residue was purified by HPLC (10-70% acetonitrile in water, 0.1% $CF_3CO_2H$) to give the title compound (25 mg).

¹H-NMR (CD₃OD, 400 MHz): δ 7.26 (d, J=8.6 Hz, 1H); 6.94 (dd, J=2.6, 8.1 Hz, 1H);
6.81 (m, 1H); 6.67 (dd, J=4.1, 8.7 Hz, 1H); 6.54 (d, J=2.5 Hz, 1H); 6.45 (dd, J=2.5, 8.6 30 Hz, 1H); 4.35 (dd, J=3.4, 10.9 Hz, 1H); 4.20 (dd, J=5.9, 10.9 Hz, 1H); 4.05 (m, 1H); 3.30-3.00 (m, 8H); 2.15 (s, 3H); 2.12-2.01 (m, 4H).

APCI-MS: m/z 430(MH⁺).

Example 5

N-(2-{[(2S)-2-Amino-3-(1'H,3H-spiro[1-benzofuran-2,4'-piperidin]-1'-yl)propyl]oxy}-4-methoxyphenyl)acetamide Step I (2R)-1-(5-Methoxy-2-nitrophenoxy)-3-(1'H,3H-spiro[1-benzofuran-2,4'-piperidin]-1'-yl)propan-2-ol A mixture of 3H-spiro[1-benzofuran-2,4'-piperidine]¹ (335 mg, 1.77 mmol) and (2R)-2-[(5-methoxy-2-nitrophenoxy)methyl]oxirane (400 mg, 1.77 mmol) in ethanol (5 mL) was stirred at 88° C. for 5 hours. The volatiles were removed in vacuo and the residue was purified by silica gel flash chromatography (0-2% methanol in dichloromethane, 0.2% NH₄OH) to give the sub-title compound (533 mg).

¹H-NMR (CDCl₃, 400 MHz): δ 8.02 (d, J=9.1 Hz, 1H); 7.16 (d, J=7.7 Hz, 1H); 7.12 (d, J=7.5 Hz, 1H); 6.84 (m, 1H); 6.77 (d, J=8.0 Hz, 1H); 6.57 (d, J=2.5 Hz, 1H); 6.54 (dd, J=2.5, 9.1 Hz, 1H); 4.28-4.12 (m, 3H); 3.89 (s, 3H); 3.02 (s, 2H); 2.96 (m, 1H); 2.90-2.64 (m, 5H); 2.04 (m, 2H); 1.89 (m, 2H).

APCI-MS: m/z 415(MH⁺).

[1]: Reference; Effland, R. R; Gardner, B. A; Strupczewski, J.J. Heterocyclic Chem. 1981, 18, 811-814.

Step II

N-(2-{[(2R)-2-hydroxy-3-(1'H,3H-spiro[1-benzofuran-2,4'-piperidin]-1'-yl)propyl]oxy}-4-methoxyphenyl)acetamide (2R)-1-(5-methoxy-2-nitrophenoxy)-3-(1'H,3H-spiro[1-benzofuran-2,4'-piperidin]-1'-yl)propan-2-ol (530 mg, 1.28 mmol) was hydrogeneted at atmospheric pressure and room temperature in the presence of Pt/C (5%, 100 mg) in ethyl acetate (30 mL) for 4 hours. Acetic anhydride (0.182 mL, 1.92 mmol) was added and the mixture was stirred at room temperature for 2 hours. The catalyst was filtered off and the filtrate was concentrated. The residue was dissolved in methanol (10 mL), conc. aqueous NaOH (4 drops) was added and the mixture was stirred at room temperature for 20 hours. The pH of the mixture was adjusted to 2 by addition of aqueous HCl. The volatiles were removed in vacuo and the residue was purified by silica gel flash chromatography (0-3% methanol in dichloromethane, 0.2% NH₄OH) to give sub-title compound (466 mg).

¹H-NMR (CD₃OD, 400 MHz): δ 7.74 (d, J=8.8 Hz, 1H); 7.12 (d, J=7.3 Hz, 1H); 7.06 (t, J=7.9 Hz, 1H); 6.78 (t, J=7.3 Hz, 1H); 6.68 (d, J=7.9 Hz, 1H); 6.61 (d, J=2.8 Hz, 1H); 6.51 (dd, J=2.6, 8.8 Hz, 1H); 4.18 (m, 1H); 4.10 (dd, J=3.4, 10.0 Hz, 1H); 3.97 (dd, J=6.3, 10.0 Hz, 1H); 3.78 (s, 3H); 3.01 (s, 2H); 2.72 (br.s, 4H); 2.62 (m, 2H); 2.15 (s, 3H); 1.94 (m, 2H); 1.84 (m, 2H).

APCI-MS: m/z 427(MH⁺).

Step III

N-(2-{[(2S)-2-Amino-3-(1'H,3H-spiro[1-benzofuran-2,4'-piperidin]-1'-yl)propyl]oxy}-4-methoxyphenyl)acetamide To a mixture of N-(2-{[(2R)-2-hydroxy-3-(1'H,3H-spiro[1-benzofuran-2,4'-piperidin]-1'-yl)propyl]oxy}-4-methoxyphenyl)acetamide (460 mg, 1.08 mmol), triphenylphosphine (566 mg, 2.16 mmol) and di-tert-butyl imidodicarbonate (469 mg, 2.16 mmol) in THF (5 mL) was added DEAD (376 mg, 2.16 mmol) in THF (3 mL) dropwise at 0° C. After addition was completed, the reaction mixture was stirred at room temperature over night. The volatiles were removed in vacuo and the residue was treated with aqueous trifluoroacetic acid (0.4 mL of H₂O in 7.6 mL of CF₃CO₂H) at room temperature for 15 minutes. The volatiles were removed in vacuo and the residue was purified by silica gel flash chromatography (0-3% methanol in dichloromethane, 0.2% NH₄OH) to give the title compound (85 mg).

¹H-NMR (CD₃OD, 400 MHz): δ 7.65 (d, J=8.8 Hz, 1H); 7.13 (d, J=7.3 Hz, 1H); 7.05 (t, J=7.9 Hz, 1H); 6.78 (t, J=7.3 Hz, 1H); 6.67 (d, J=7.9 Hz, 1H); 6.60 (d, J=2.6 Hz, 1H); 6.50 (dd, J=2.6, 8.8 Hz, 1H); 4.11 (dd, J=3.4, 9.7 Hz, 1H); 3.91 (dd, J=6.5, 9.7 Hz, 1H); 3.78 (s, 3H); 3.40 (m, 1H); 3.01 (s, 2H); 2.78-2.48 (m, 6H); 2.15 (s, 3H); 1.94 (m, 2H); 1.84 (m, 2H).

APCI-MS: m/z 426(MH⁺).

From this reaction mixture, N-{2-[3-Amino-2-(1'H,3H-spiro[1-benzofuran-2,4'-piperidin]-1'-yl)propoxy]-4-methoxyphenyl}acetamide (55 mg) was also obtained as byproduct, see example 10.

Example 6

N-(2-{[(2S)-2-Amino-3-(1'H,3H-spiro[1-benzofuran-2,4'-piperidin]-1'-yl)propyl]oxy}-4-hydroxyphenyl)acetamide bis(trifluoroacetate) (salt)

To a cold (ice-water) solution of N-(2-{[(2S)-2-amino-3-(1'H,3H-spiro[1-benzofuran-2,4'-piperidin]-1'-yl)propyl]oxy}-4-methoxyphenyl)acetamide (75 mg, 0.176 mmol) in CH₂Cl₂ (3 mL) was added a solution of BBr₃ in CH₂Cl₂ (1 M, 1.0 mL, 1.0 mmol) slowly under nitrogen atmosphere. After the addition was completed, the reaction mixture was stirred at 0° C. for 3.5 hours, methanol (2 mL) was added slowly and stirring was continued at 0° C. for 20 minutes. The volatiles were removed in vacuo and the residue was dissolved in methanol (5 mL), concentrated aqueous NH₄OH (1 mL) was added and after 5 minutes the volatiles were removed in vacuo and the residue was purified by HPLC (10-55% acetonitrile in water, 0.1% CF₃CO₂H) to give the title compound (45 mg).

¹H-NMR (CD₃OD, 400 MHz): δ 7.27 (d, J=8.6 Hz, 1H); 7.17 (d, J=7.3 Hz, 1H); 7.08 (t, J=7.6 Hz, 1H); 6.84 (t, J=7.3 Hz, 1H); 6.72 (d, J=8.0 Hz, 1H); 6.53 (d, J=2.4 Hz, 1H);
6.44 (dd, J=2.5, 8.6 Hz, 1H); 4.35 (dd, J=3.5, 10.9 Hz, 1H); 4.19 (dd, J=5.8, 10.9 Hz, 1H); 4.05 (m, 1H); 3.30-3.00 (m, 8H); 2.16 (s, 3H); 2.08 (m, 4H).

APCI-MS: m/z 412(MH⁺).

Example 7

N-(2-{[(2S)-2-(Acetylamino)-3-(5-fluoro-1'H,3H-spiro[1-benzofuran-2,4'-piperidin]-1'-yl)propyl]oxy}-4-methoxyphenyl)acetamide To a solution of N—(2-{[(2S)-2-amino-3-(5-fluoro-1'H,3H-spiro[1-benzofuran-2,4'-piperidin]-1'-yl)propyl]oxy}-4- methoxyphenyl)acetamide (13 mg, 0.029 mmol) in THF (1.5 mL) was added pyridine (0.3 mL) followed by acetic anhydride (0.15 mL) and the mixture was stirred at room temperature for 2 hours. Then 0.5 mL H$_2$O was added and the mixture was stirred at room temperature for 30 minutes. The volatiles were removed in vacuo and co-evaporated with toluene. The residue was dissolved in methanol (3 mL) and pH was adjusted to 14 by addition of aqueous 3M NaOH. The volatiles were removed in vacuo and the residue was purified by silica gel flash chromatography (0-1.5% methanol in dichloromethane, 0.2% NH$_4$OH) to give the title compound (9 mg).

$^1$H-NMR (CD$_3$OD, 400 MHz): δ 7.63 (d, J=8.8 Hz, 1H); 6.89 (dd, J=2.6, 8.3 Hz, 1H);

6.77 (m, 1H); 6.64-6.59 (m, 2H); 6.50 (dd, J=2.6, 8.8 Hz, 1H); 4.47 (m, 1H); 4.10 (dd, J=4.3, 9.6 Hz, 1H); 4.05 (dd, J=5.7, 9.6 Hz, 1H); 3.78 (s, 3H); 3.00 (s, 2H); 2.74-2.52 (m, 6H); 2.16 (s, 3H); 2.02 (s, 3H); 1.93 (m, 2H); 1.81 (m, 2H).

APCI-MS: m/z 486(MH$^+$).

Example 8

N-{2-[3-Amino-2-(5-chloro-1'H,3H-spiro[1-benzofuran-2,4'-piperidin]-1'-yl)propoxy]-4-methoxyphenyl}acetamide bis(trifluoroacetate)

After flash chromatography on silica gel (from Example 1, step IV) this compound was purified by HPLC (10-65% CH$_3$CN in H$_2$O, 0.1% CF$_3$CO$_2$H) to give the title compound (95 mg).

$^1$H-NMR (CD$_3$OD, 400 MHz): δ 7.28 (d, J=8.7 Hz, 1H); 7.14 (m, 1H); 7.04 (dd, J=2.2, 8.5 Hz, 1H); 6.71-6.66 (m, 2H); 6.57 (dd, J=2.5, 8.7 Hz, 1H); 4.34 (d, J=5.0 Hz, 2H);

3.79 (s, 3H); 3.54 (m, 1H); 3.42-3.24 (m, 2H); 3.18-2.95 (m, 6H); 2.13 (s, 3H); 2.02 (m, 4H).

APCI-MS: m/z 460(MH$^+$).

Example 9

N-{2-[3-Amino-2-(5-fluoro-1'H,3H-spiro[1-benzofuran-2,4'-piperidin]-1'-yl)propoxy]-4-methoxyphenyl}acetamide bis(trifluoroacetate)

After flash chromatography on silica gel this compound, (from Example 3, step IV) was purified by HPLC (10-70% CH$_3$CN in H$_2$O, 0.1% CF$_3$CO$_2$H) to give the title compound (16 mg).

$^1$H-NMR (CD$_3$OD, 400 MHz): δ 7.30 (d, J=8.6 Hz, 1H); 6.92 (dd, J=2.7, 8.2 Hz, 1H);

6.82-6.75 (m, 1H); 6.69-6.64 (m, 2H); 6.57 (dd, J=2.6, 8.7 Hz, 1H); 4.34-4.23 (m, 2H);

3.82 (s, 3H); 3.42 (m, 1H); 3.22 (m, 2H); 3.08-2.79 (m, 6H); 2.13 (s, 3H); 2.07-2.84 (m, 4H).

APCI-MS: m/z 444(MH$^+$).

Example 10

N-{2-[3-Amino-2-(1'H,3H-spiro[1-benzofuran-2,4'-piperidin]-1'-yl)propoxy]-4-methoxyphenyl}acetamide bis(trifluoroacetate)

After flash chromatography on silica gel this compound, (from Example 5, step III), was purified by HPLC (10-65% CH$_3$CN in H$_2$O, 0.1% CF$_3$CO$_2$H) to give the title compound (55 mg).

$^1$H-NMR (CD$_3$OD, 400 MHz): δ 7.30 (d, J=8.7 Hz, 1H); 7.15 (d, J=7.2 Hz, 1H); 7.07 (t, J=7.4 Hz, 1H); 6.81 (t, J=7.3 Hz, 1H); 6.71 (d, J=7.9 Hz, 1H); 6.68 (d, J=2.6 Hz, 1H); 6.58 (dd, J=2.6, 8.7 Hz, 1H); 4.32 (m, 2H); 3.81 (s, 3H); 3.48 (m, 1H); 3.40-3.22 (m, 2H);

3.14-2.88 (m, 6H); 2.13 (s, 3H); 2.00 (m, 4H).

APCI-MS: m/z 426(MH$^+$).

Example 11

N-{2-[3-Amino-2-(5-chloro-1'H,3H-spiro[1-benzofuran-2,4'-piperidin]-1'-yl)propoxy]phenyl}urea bis(trifluoroacetate)

Step I

N-(2-Hydroxyphenyl)urea

2-Aaminophenol (1.09 g, 10.0 mmol) was dissolved in aqueous HCl (1 M, 10 mL), then ammonium acetate was added until pH became 5, potassium isocyanate (892 mg, 11.0 mmol) in H$_2$O (3 mL) was added with vigorous stiring at room temperature. After addition was completed the reaction mixture was stirred at room temperature over night. The precipitate was filtered off, washed with water and the precipitate was collected to give the sub-title compound (1.3 g).

$^1$H-NMR (DMSO-d$_6$, 400 MHz): δ 10.00 (br.s, 1H); 8.00 (br.s, 1H); 7.80 (d, J=8.0 Hz, 1H); 6.80-6.65 (m, 3H); 6.22 (br.s, 2H).

APCI-MS: m/z 153(MH$^+$).

Step II

N-{2-[(2R)-Oxiran-2-ylmethoxy]phenyl}urea

To a mixture of (2S)-oxiran-2-ylmethanol (296 mg, 4.0 mmol), N-(2-hydroxyphenyl)urea (609 mg, 4.0 mmol) and triphenylphosphine (1.05 g, 4.0 mmol) in THF (10 mL) was dropwise added DEAD (697 mg, 4.0 mmol) in THF (3 mL) at room temperature. After addition was completed the reaction mixture was stirred at room temperature over night. The volatiles were removed in vacuo and the residue was purified by silica gel flash chromatography (0-80% ethyl acetate in petroleum spirit) to give sub-title compound (336 mg).

$^1$H-NMR (DMSO-d$_6$, 400 MHz): δ 8.08 (m, 1H); 7.82 (s, 1H); 6.98 (m, 1H); 6.85 (m, 2H); 6.24 (br.s, 2H); 4.37 (dd, J=2.5, 11.7 Hz, 1H); 3.89 (dd, J=6.6, 11.7 Hz, 1H); 3.38 (m, 1H); 2.87 (t, J=4.7 Hz, 1H); 2.75 (dd, J=2.7, 5.0 Hz, 1H).

Step III

N-(2-{[(2R)-3-(5-Chloro-1'H,3H-spiro[1-benzofuran-2,4'-yl)-2-hydroxypropyl]oxy}phenyl)urea A mixture of 5-chloro-3H-spiro[1-benzofuran-2,4'-piperidine] (161 mg, 0.72 mmol) and N-{2-[(2R)-oxiran-2-ylmethoxy]phenyl}urea (150 mg, 0.72 mmol) in ethanol (2 mL) was stirred at 88° C. for 5 hours. The volatiles were removed in vacuo and the residue was purified by silica gel flash chromatography (0-2% methanol in dichloromethane, 0.2% NH$_4$OH) to give the sub-title compound (220 mg).

$^1$H-NMR (CD$_3$OD, 400 MHz): δ 7.95 (m, 1H); 7.14 (m, 1H); 7.04 (dd, J=2.2, 8.4 Hz, 1H); 7.00-6.86 (m, 3H); 6.66 (d, J=8.5 Hz, 1H); 4.23-4.16 (m, 1H); 4.09 (dd, J=3.8, 9.9 Hz, 1H); 4.00 (dd, J=6.1, 9.9 Hz, 1H); 3.02 (s, 2H); 2.78-2.55 (m, 6H); 1.94 (m, 2H); 1.84 (m, 2H).

APCI-MS: m/z 432(MH$^+$).

Step IV

N-{2-[3-Amino-2-(5-chloro-1'H,3H-spiro[1-benzo-furan-2,4'-piperidin]-1'-yl)propoxy]phenyl}urea bis (trifluoroacetate)

To a mixture of N—(2-{[(2R)-3-(5-chloro-1'H,3H-spiro[1-benzofuran-2,4'-piperidin]-1'-yl)-2-hydroxypropyl]oxy}phenyl)urea (190 mg, 0.439 mmol), triphenylphosphine (173 mg, 0.658 mmol) and di-tert-butyl imidodicarbonate (143 mg, 0.658 mmol) in THF (3 mL) was added DEAD (115 mg, 0.658 mmol) in THF (2 mL) dropwise at 0° C. After addition was completed, the reaction mixture was stirred at room temperature over night. The volatiles were removed in vacuo and the residue was treated with aqueous trifluoroacetic acid (0.2 mL of $H_2O$ in 3.8 mL of $CF_3CO_2H$) at room temperature for 20 minutes. The volatiles were removed in vacuo and the residue was purified by HPLC (10-70% $CH_3CN$ in $H_2O$, 0.1% $CF_3CO_2H$) to give the title compound (10 mg).

$^1$H-NMR (CD$_3$OD, 400 MHz): δ 7.63 (m, 1H); 7.17-6.95 (m, 5H); 6.68 (d, J=8.4 Hz, 1H); 4.44-4.28 (m, 2H); 3.50 (m, 1H); 3.31 (m, 3H); 3.18-2.87 (m, 5H); 2.02 (m, 4H).

APCI-MS: m/z 431 (MH$^+$).

Example 12

N-{2-[3-Amino-2-(5-fluoro-1'H,3H-spiro[1-benzo-furan-2,4'-piperidin]-1'-yl)propoxy]phenyl}urea bis (trifluoroacetate)

Step I

N-(2-{[(2R)-3-(5-Fluoro-1'H,3H-spiro[1-benzofuran-2,4'-piperidin]-1'-yl)-2-hydroxypropyl]oxy}phenyl)urea 5-fluoro-3H-spiro[1-benzofuran-2,4'-piperidine] (182 mg, 0.88 mmol) and N-{2-[(2R)-oxiran-2-ylmethoxy]phenyl}urea (183 mg, 0.88 mmol) in ethanol (2 mL) was stirred at 88° C. over night. The volatiles were removed in vacuo and the residue was purified by silica gel flash chromatography (0-2% methanol in dichloromethane, 0.2% NH$_4$OH) to give the sub-title compound (250 mg).

$^1$H-NMR (CD$_3$OD, 400 MHz): δ 7.94 (m, 1H); 7.00-6.87 (m, 4H); 6.78 (m, 1H); 6.63 (dd, J=4.2, 8.8 Hz, 1H); 4.23-4.16 (m, 1H); 4.10 (dd, J=3.8, 9.9 Hz, 1H); 4.00 (dd, J=6.1, 9.9 Hz, 1H); 3.02 (s, 2H); 2.78-2.55 (m, 6H); 1.93 (m, 2H); 1.83 (m, 2H).

APCI-MS: m/z 416(MH$^+$).

Step II

N-{2-[3-Amino-2-(5-fluoro-1'H,3H-spiro[1-benzo-furan-2,4'-piperidin]-1'-yl)propoxy]phenyl}urea bis (trifluoroacetate)

To a mixture of N—(2-{[(2R)-3-(5-fluoro-1'H,3H-spiro[1-benzofuran-2,4'-piperidin]-1'-yl)-2-hydroxypropyl]oxy}phenyl)urea (200 mg, 0.48 mmol), triphenylphosphine (189 mg, 0.72 mmol) and di-tert-butyl imidodicarbonate (156 mg, 0.72 mmol) in THF (3 mL) was added DEAD (125 mg, 0.72 mmol) in THF (2 mL) dropwise at 0° C. After addition was completed, the reaction mixture was stirred at room temperature over night. The volatiles were removed in vacuo and the residue was treated with aqueous trifluoroacetic acid (0.2 mL of $H_2O$ in 3.8 mL of $CF_3CO_2H$) at room temperature for 20 minutes. The volatiles were removed in vacuo and the residue was purified by HPLC (10-70% $CH_3CN$ in $H_2O$, 0.1% $CF_3CO_2H$) to give the title compound (15 mg).

$^1$H-NMR (CD$_3$OD, 400 MHz): δ 7.63 (dd, J=1.2, 8.0 Hz, 1H); 7.15-7.05 (m, 2H); 6.97 (m, 1H); 6.91 (dd, J=2.6, 8.2 Hz, 1H); 6.78 (m, 1H); 6.65 (dd, J=4.2, 8.8 Hz, 1H); 4.37 (dd, J=5.5, 10.7 Hz, 1H); 4.28 (m, 1H); 3.43 (m, 1H); 3.30 (m, 3H); 3.17-2.78 (m, 5H); 2.07-1.88 (m, 4H).

APCI-MS: m/z 415(MH$^+$).

Example 13

N-{2-[2-Chloro-3-(5-chloro-1'H,3H-spiro[1-benzo-furan-2,4'-piperidin]-1'-yl)propoxy]-4-hydroxyphenyl}acetamide trifluoroacetate (salt)

Step I (1Z)-1-(2,4-Dihydroxyphenyl)ethanone oxime 1-(2,4-Dihydroxyphenyl)ethanone (4.5 g, 29.6 mmol) was dissolved in pyridine (17 mL). Hydroxylamine hydrochloride (2.1 g, 29.6 mmol) was added in small portions over 10 minutes. The reaction mixture was stirred at room temperature over night, partitioned between ethyl acetate and $H_2O$. The organic layer was washed with $H_2O$ and 0.2 M aqueous HCl respectively. The oily residue was treated with $H_2O$, evaporated in vacuo to yield a white semi-solid residue which was treated with toluene and then evaporated in vacuo to give the sub-title compound (4.8 g) as a white solid.

APCI-MS: m/z 168(MH$^+$).

Step II

2-Methyl-1,3-benzoxazol-6-ol

To a cooled (ice-water) solution of (1Z)-1-(2,4-dihydroxyphenyl)ethanone oxime (9.7 g, 57.7 mmol) and dimethylacetamide (11 mL) in acetonitrile (65 mL) was added phosphorous oxychloride (5.6 mL, 60.3 mmol) dropwise. The temperature was not allowed to exceed 10° C. during the reaction. After 1 hour stirring at room temperature the yellow slurry was poured into a mixture of aqueous NaHCO$_3$ and ice. The resulting precipitate was filtered off and dried to give the sub-title compound (6.3 g).

$^1$H-NMR (DMSO-d$_6$, 400 MHz): δ 9.68 (br.s, 1H); 7.38 (d, J=8.5 Hz, 1H); 6.94 (d, J=2.2 Hz, 1H); 6.74 (dd, J=8.5, 2.2 Hz, 1H); 2.50 (s, 3H).

APCI-MS: m/z 150(MH$^+$).

Step III

2-Methyl-1,3-benzoxazol-6-yl acetate

A slurry of 2-methyl-1,3-benzoxazol-6-ol (7.1 g, 48.7 mmol) in THF (150 mL) was cooled to 10° C. and triethylamine (11.3 mL, 81.3 mmol) was added in one portion, followed by the addition of acetyl chloride (5.8 mL, 81.3 mmol) in small portions. After addition was completed the reaction mixture was stirred at room temperature over night, partitioned between ethyl acetate and water. The organic layer was dried over Na$_2$SO$_4$, filtered and concentrated in vacuo to give sub-title compound (8.2 g).

$^1$H-NMR (DMSO-d$_6$, 400 MHz): δ 7.65 (d, 1H); 7.47 (s, 1H); 7.15 (d, 1H); 2.60 (s, 3H); 2.24 (s, 3H).

Step IV

4-(Acetylamino)-3-hydroxyphenyl acetate

To a solution of 2-methyl-1,3-benzoxazol-6-yl acetate (5.05 g, 28.8 mmol) in THF (100 mL) a mixture of trifluoroacetic acid/water (4 mL/10 mL) was added. The reaction mixture was stirred at room temperature for 16 hours, saturated aqueous NaHCO$_3$ (150 mL) was added. The mixture was extracted with ethyl acetate, dried over Na$_2$SO$_4$, filtered and concentrated in vacuo to give sub-title compound (4.0 g) as a crude product.

Step V

4-(acetylamino)-3-[(2S)-oxiran-2-ylmethoxy]phenyl acetate

A mixture of 4-(acetylamino)-3-hydroxyphenyl acetate (669 mg, 3.2 mmol), (2S)-oxiran-2-ylmethyl 3-nitrobenzenesulfonate (748 mg, 2.9 mmol) and Cs$_2$CO$_3$ ((1.05 g, 3.2 mmol) in 1-methyl-pyrrolidinone (10 mL) was stirred at room temperature over night. The reaction mixture was partitioned between ethyl acetatwe and water. The organic layer was dried over Na$_2$SO$_4$, filtered and concentrated in vacuo to give a yellow oil which was suspended in methanol/diethyl ether. The precipitate was filtered off and dried to give the sub-title compound (296 mg).

$^1$H-NMR (CDCl$_3$, 400 MHz): δ 8.40 (d, 1H); 7.80 (s, 1H); 6.78 (m, 2H); 4.39 (m, 1H); 3.92 (m, 1H); 3.40 (m, 1H); 2.98 (t, 1H); 2.80 (m, 1H); 2.25 (s, 3H); 2.20 (s, 3H).

Step VI

N-(2-{[(2S)-3-(5-Chloro-1'H,3H-spiro[1-benzofuran-2,4'-piperidin]-1'-yl)-2-hydroxypropyl]oxy}-4-hydroxyphenyl)acetamide 5-Chloro-3H-spiro[1-benzofuran-2,4'-piperidine] (335.5 mg, 1.5 mmol) and 4-(acetylamino)-3-[(2S)-oxiran-2-ylmethoxy]phenyl acetate (398 mg, 1.5 mmol) in ethanol (3 mL) was stirred at 80° C. for 24 hours. The volatiles were removed in vacuo and the residue was purified by silica gel flash chromatography (0-3% methanol in dichloromethane, 0.2% NH$_4$OH) to give the sub-title compound (302 mg).

$^1$H-NMR (CD$_3$OD, 400 MHz): δ 7.57 (d, J=8.7 Hz, 1H); 7.14 (s, 1H); 7.04 (dd, J=2.3, 8.5 Hz, 1H); 6.65 (d, J=8.5 Hz, 1H); 6.48 (d, J=2.5 Hz, 1H); 6.36 (dd, J=2.6, 8.7 Hz, 1H); 4.20-4.13 (m, 1H); 4.05 (dd, J=3.4, 9.8 Hz, 1H); 3.93 (dd, J=6.2, 9.8 Hz, 1H); 3.02 (s, 2H); 2.77-2.55 (m, 6H); 2.14 (s, 3H); 1.93 (m, 2H); 1.84 (m, 2H).

APCI-MS: m/z 447(MH$^+$).

Step VII

N-{2-[2-Chloro-3-(5-chloro-1'H,3H-spiro[1-benzofuran-2,4'-piperidin]-1'-yl)propoxy]-4-hydroxyphenyl}acetamide trifluoroacetate (salt)

To a solution of oxalyl chloride (22 mg, 0.173 mmol) in dichloromethane (1 mL) was added a solution of DMSO (26 mg, 0.332 mmol) in dichloromethane (0.5 ML) slowly at −78° C. After 10 minutes a solution of N-(2-{[(2S)-3-(5-chloro-1'H,3H-spiro[1-benzofuran-2,4'-piperidin]-1'-yl)-2-hydroxypropyl]oxy}-4-hydroxyphenyl)acetamide (25 mg, 0.056 mmol) in dichloromethane (0.5 mL) was added slowly. After 25 minutes a solution of diethylaminosulfur trifluoride (DAST) (0.1 mL) in dichloromethane (0.5 mL) was added slowly and the reaction mixture was stirred at −78° C. for 4 hours, Et$_3$N (0.2 mL) was added and after 5 minutes cooling bath was removed and the reaction mixture was diluted by addition of dichloromethane (5 mL), washed with water. The organic layer was dried over Na$_2$SO$_4$, filtered and concentrated in vacuo. The residue was purified by HPLC (10-70% CH$_3$CN in H$_2$O, 0.1% CF$_3$CO$_2$H) to give the title compound as a byproduct (2 mg).

$^1$H-NMR (CD$_3$OD, 400 MHz): δ 7.32 (d, J=8.7 Hz, 1H); 7.15 (s, 1H); 7.06 (dd, J=2.2, 8.5 Hz, 1H); 6.68 (d, J=8.5 Hz, 1H); 6.51 (d, J=2.5 Hz, 1H); 6.41 (dd, J=2.5, 8.6 Hz, 1H); 4.54 (br.s, 1H); 4.28 (d, J=5 Hz, 2H); 3.24-2.83 (m, 8H); 2.13 (s, 3H); 1.98 (m, 4H).

APCI-MS: m/z 465(MH$^+$).

Example 14

N-{2-[2-(5-Chloro-1'H,3H-spiro[1-benzofuran-2,4'-piperidin]-1'-yl)propoxy]-4-methoxyphenyl}acetamide trifluoroacetate Step I

N-[2-(2-Hydroxypropoxy)-4-methoxyphenyl]acetamide

This was obtained during reaction in Example 3, Step II, as a byproduct (204 mg). $^1$H-NMR (CDCl$_3$, 400 MHz): δ 8.02 (d, J=8.6 Hz, 1H); 7.85 (br.s, 1H); 6.48 (m, 2H); 4.22 (m, 1H); 3.98 (dd, J=2.9, 9.9 Hz, 1H); 3.84 (m, 1H); 3.78 (s, 3H); 2.15 (s, 3H); 1.29 (d, J=6.5 Hz, 3H).

APCI-MS: m/z 240(MH$^+$).

Step II

N-{2-[2-(5-Chloro-1'H,3H-spiro[1-benzofuran-2,4'-piperidin]-1'-yl)propoxy]-4-methoxyphenyl}acetamide N-[2-(2-Hydroxypropoxy)-4-methoxyphenyl]acetamide (92 mg, 0.38 mmol) was dissolved in dichloromethane (3 mL), cooled to 0° C. and Et$_3$N (0.076 mL, 0.547 mmol) was added followed by methanesulfonyl chloride (52 mg, 0.456 mmol). The reaction mixture was stirred at 0° C. for 2 hours, diluted by addition of dichloromethane (20 mL), washed successively with saturated aqueous NaHCO$_3$ and H$_2$O. The organic layer was dried over Na$_2$SO$_4$, filtered and concentrated in vacuo. The residue was taken in ethanol (3 mL), 5-chloro-3H-spiro[1-benzofuran-2,4'-piperidine] (85 mg, 0.38 mmol) was added and the mixture was refluxed for 40 h. The reaction mixture was cooled to room temperature and the volatiles were removed in vacuo. The residue was dissolved in ethyl acetate (30 mL), washed succesively with saturated aqueous NaHCO$_3$ and water, dried over Na$_2$SO$_4$, filtered and concentrated in vacuo. The residue was purified by HPLC (10-70% CH$_3$CN in H$_2$O, 0.1% CF$_3$CO$_2$H) to give the title compound (35 mg).

$^1$H-NMR (CD$_3$OD, 400 MHz): δ 7.20 (m, 1H); 7.18 (d, J=8.6 Hz, 1H); 7.11 (dd, J=2.1, 8.5 Hz, 1H); 6.77 (d, J=8.5 Hz, 1H); 6.71 (d, J=2.6 Hz, 1H); 6.61 (dd, J=2.6, 8.7 Hz, 1H); 4.46 (dd, J=3.4, 12.2 Hz, 1H); 4.36 (dd, J=8.6, 12.2 Hz, 1H); 3.96 (m, 1H); 3.81 (s, 3H); 3.69-3.40 (m, 4H); 3.12 (s, 2H); 2.45-2.17 (m, 4H); 1.50 (d, J=7.0 Hz, 3H).

APCI-MS: m/z 445(MH$^+$).

Example 15

5-{[(2S-2-Amino-3-(5-fluoro-1'H,3H-spiro[1-benzofuran-2,4'-piperidin]-1'-yl)propyl]oxy}-2H-1,4-benzoxazin-3(4H)-one Step I:

2-Aminobenzene-1,3-diol

A mixture of 2-nitrobenzene-1,3-diol (5 g, 32.2 mmol) and 10% Pd on charcoal (230 mg) in ethanol (100 ml) were hydrogenated with $H_2$ at atmospheric pressure overnight. The reaction mixture was filtered through celite. Ethanol was removed by evaporation to yield the subtitled compound (4 g, 99%).

$^1$H-NMR (400 MHz, DMSO-$d_6$): δ 8.81 (br.s, 2H), 6.24 (m, 3H), 3.81 (br.s, 2H).

APCI-MS: m/z 126.0 (MH$^+$).

Step II:

2-Chloro-N—(2,6-dihydroxyphenyl)acetamide $KH_2PO_4$ (17.2 g, 126.3 mmol) and $K_2HPO_4$ (8.2 g, 35.7 mmol) in 188 ml of distilled water were deoxygenated by passing argon through the mixture for 0.5 hour. 2-Aminobenzene-1,3-diol (1 g, 8.0 mmol) was added to the buffer solution and chloroacetyl chloride (0.64 ml, 8.0 mmol) was added slowly to the reaction mixture. After addition was completed, the reaction mixture was stirred at room temperature for 1.5 hours. Water was removed by freeze-drying and the residue was dissolved in 20% MeOH in DCM. The insoluble salt was removed by filtration, the solvent was evaporated to give the subtitled compound which was used without purification in the next step.

APCI-MS: m/z 202.0 (MH$^+$).

Step III:

5-Hydroxy-2H-1,4-benzoxazin-3(4R)-one

2-Chloro-N—(2,6-dihydroxyphenyl)acetamide (1.99 g, 9.88 mmol) was dissolved in 150 ml of 10% aqueous $K_2CO_3$ and the solution was heated to 40° C. for 45 minutes. After cooling and neutralization with 2M HCl the reaction mixture was extracted with ethyl acetate. Drying with $MgSO_4$ and evaporation of solvent afforded crude material (0.54 g, overall yield from Steps II and III 41%).

APCI-MS: m/z 166.0 (MH$^+$).

Step IV

Methyl N-(tert-butoxycarbonyl)-3-(5-fluoro-1'H,3H-spiro[1-benzofuran-2,4'-piperidin]-1'-yl)-L-alanine To a cold (ice-water bath) suspension of 5-fluoro-3H-spiro[1-benzofuran-2,4'-piperidine] (1.03 g, 5 mmol) and methyl N—(tert-butoxycarbonyl)-3-iodo-L-alanate (1.64 g, 5 mmol) in dichloromethane (20 mL) was added triethyl amine (0.697 mL, 5 mmol). After a clear solution was obtained, the reaction mixture was kept at 5° C. for 48 h. Then it was diluted by addition of dichloromethane (50 mL), washed with water (10 mL), dried over $Na_2SO_4$, filtered and concentrated in vacuo. The residue was purified by silica gel flash chromatography (0-1.5% methanol in dichloromethane containing 0.2% ammonia) to give the subtitle compound (1.2 g).

$^1$H-NMR (CDCl$_3$, 400 MHz): δ 6.85 (m, 1H); 6.78 (m, 1H); 6.64 (dd, J=4.2, 8.7 Hz, 1H);
5.40 (br.s, 1H); 4.35 (br.s, 1H); 3.76 (s, 3H); 2.99 (s, 2H); 2.80-2.43 (m, 6H); 1.93 (m, 2H);
1.77 (m, 2H); 1.48 (s, 9H).

APCI-MS: m/z 409 (MH$^+$).

Step V tert-Butyl [(1)-2-(5-fluoro-1'H,3H-spiro[1-benzofuran-2,4'-piperidin]-1'-yl)-1-(hydroxymethyl)ethyl]carbamate To a suspension of LiBH$_4$ (77 mg, 3.51 mmol) in THF (10 mL) was added a solution of methyl N-(tert-butoxycarbonyl)-3-(5-fluoro-1'H,3H-spiro[1-benzofuran-2,4'-piperidin]-1'-yl)-L-alanine (1.2 g, 2.93 mmol) in THF (15 mL) at 0° C. After the addition was completed, stirring was continued at 0° C. for 4 h, then at room temperature over night. The reaction mixture was cooled again to 0° C., and a saturated aqueous NH$_4$Cl solution (15 mL) was added slowly. After 1 h, the reaction mixture was extracted with ethyl acetate. The combined organic layer was washed with water (10 mL), dried over Na$_2$SO$_4$, filtered and concentrated. The residue was purified by silica gel flash chromatography (0-1.5% methanol in dichloromethane containing 0.2% ammonia) to give title compound (376 mg).

$^1$H-NMR (CD$_3$OD, 400 MHz): δ 6.90 (m, 1H); 6.77 (m, 1H); 6.62 (dd, J=4.2, 8.7 Hz, 1H); 3.78 (m, 1H); 3.56 (m, 2H); 3.00 (s, 2H); 2.68 (br.s, 4H); 2.50 (m, 2H); 1.94 (m, 2H); 1.82 (m, 2H); 1.48 (s, 9H).

APCI-MS: m/z 381 (MH$^+$).

Step VI

(2S)-2-[(tert-butoxycarbonyl)amino]-3-(5-fluoro-1'H,3H-spiro[1-benzofuran-2,4'-piperidin]-1'-yl)propyl 3-nitrobenzenesulfonate To a stirred solution of tert-butyl [(1S)-2-(5-fluoro-1'H,3H-spiro[1-benzofuran-2,4'-piperidin]-1'-yl)-1-(hydroxymethyl)ethyl]carbamate (300 mg, 0.79 mmol) in DCM (20 ml) was added triethylamine (120 mg, 1.18 mmol). The mixture was cooled to 0° C., and a solution of 3-nitrobenzenesulfonyl chloride (250 mg, 1.18 mmol) in DCM (5 ml) was added. The mixture was stirred at 0° C. for 4 h, then allowed to warm to room temperature and stirred overnight. Then the reaction mixture was washed with water (30 ml) and aq. NaHCO$_3$ (1 M, 30 ml), and dried over Na$_2$SO$_4$. The solvent was removed i.vac. to afford a colourless oil (155 mg, 35%), which was used in the next step without purification.

$^1$H-NMR (400 MHz, CDCl$_3$): δ 8.73 (m, 1H), 8.30-8.21 (m, 2H), 7.58 (t, J=8.0 Hz, 1H), 7.06 (br. d, J=5.8 Hz, 1H), 6.91-6.78 (m, 2H), 6.64 (dd, J=8.7, 4.1 Hz, 1H), 5.00 (m, 2H), 4.87 (m, 1H), 4.71 (m, 1H), 4.40 (m, 2H), 3.96 (d, J=12.0 Hz, 1H), 3.64 (m, 3H), 3.07 (s, 2H), 2.16 (s, 4H), 1.41 (s, 9H)

Step VII

5-{[(2S)-2-Amino-3-(5-fluoro-1'H,3H-spiro[1-benzofuran-2,4'-piperidin]-1'-yl)propyl]oxy}-2H-1,4-benzoxazin-3(4H)-one A mixture of (2S)-2-[(tert-butoxycarbonyl)amino]-3-(5-fluoro-1'H,3H-spiro[1-benzofuran-2,4'-piperidin]-1'-yl)propyl 3-nitrobenzenesulfonate (77 mg, 0.14 mmol), 5-Hydroxy-2H-1,4-benzoxazin-3(4R)-one (23 mg, 0.14 mmol) and Cs$_2$CO$_3$ (68 mg, 0.21 mmol) in dry DMF (2 ml) was stirred at room temperature for 36 h. Then the mixture was partitionned between DCM (50 ml) and water (50 ml), and the layers were separated. The organic layer was washed with water, and the solvent was removed i.vac. The residue was dissolved in TFA (95% in water, 2 ml), and the solution was stirred at room temperature for 1 h. Then the reaction mixture was diluted with ethyl acetate (30 ml), and washed with aq. NaHCO$_3$ (1 M, 30 ml). The solvent was removed i.vac., the residue purified by HPLC (10-40% CH$_3$CN in H$_2$O, 0.6% NH$_3$) to give the title compound (12 mg, 21%).

$^1$H-NMR (CD$_3$OD, 400 MHz): δ 6.91 (m, 2H), 6.78 (td, J=8.9, 2.7 Hz, 1H), 6.68. (d, J=8.4 Hz, 2H), 6.62 (m, 2H), 4.54 (s, 2H), 4.14 (dd, J=9.6, 3.3 Hz, 1H), 3.94 (dd, J=9.5, 6.4 Hz, 1H), 3.43 (m, 1H), 3.02 (s, 2H), 2.77-2.55 (m, 4H), 2.52 (d, J=7.0 Hz, 2H), 1.95 (m, 2H), 1.85 (m, 2H).

APCI-MS: m/z 428 (MH$^+$).

Example 16

8-{[(2S)-2-Amino-3-(5-fluoro-1'H,3H-spiro[1-benzofuran-2,4'-piperidin]-1'-yl)propyl]oxy}quinolin-2(1H)-one Step I:

8-Hydroxyquinolin-2(1H)-one

Quinolin-8-ol 1-oxide (20 g, 124 mmol) in acetic anhydride (200 ml) was stirred at 90° C. for 5 hours. Then the reaction mixture was poured into water/ice mixture (1.5 L), and made neutral by addition of conc. aq. NH$_3$. The precipitate formed was collected by filtration and washed with water. The crude product was purified by suspending in propan-2-ol and addition of petroleum ether to give 2-oxo-1,2-dihydroquinolin-8-yl acetate. 2-Oxo-1,2-dihydroquinolin-8-yl acetate was heated in conc. aq. HCl (200 ml) at 90° C. for 4 hours. The reaction mixture was poured into ice-cold water (400 ml), and the precipitate formed was collected by filtration and washed with water. Recrystallization from propan-2-ol/petroleum ether afforded the subtitle compound (14.1 g, 70%).

$^1$H-NMR (400 MHz, DMSO-d$_6$): δ 10.46 (s, 1H), 10.21 (s, 1H), 7.84 (d, J=9.5 Hz, 1H), 7.10 (d, J=7.6 Hz, 1H), 7.00 (t, J=7.7 Hz, 1H), 6.95 (dd, J=7.8, 1.2 Hz, 1H), 6.48 (d, J=9.5 Hz, 1H)

APCI-MS: m/z 162 (MH$^+$).

Step II

8-{[(2S)-2-Amino-3-(5-fluoro-1'H,3H-spiro[1-benzofuran-2,4'-piperidin]-1'-yl)propyl]oxy}quinolin-2(1H)-one Prepared from 8-Hydroxyquinolin-2(1H)-one as described for 5-{[(2S)-2-Amino-3-(5-fluoro-1'H,3H-spiro[1-benzofuran-2,4'-piperidin]-1'-yl)propyl]oxy}-2H-1,4-benzoxazin-3(4H)-one (Example 15, Step VII).

$^1$H-NMR (CD$_3$OD, 400 MHz): δ 7.96 (d, J=9.4 Hz, 1H), 7.28 (dd, J=7.0, 2.1 Hz, 1H), 7.20 (m, 2H), 6.90 (dd, J=8.2, 2.6 Hz, 1H), 6.78 (td, J=8.9, 2.7 Hz, 1H), 6.65 (d, J=9.4 Hz, 1H), 6.62 (m, 1H), 4.27 (dd, J=9.6, 3.3 Hz, 1H), 4.08 (dd, J=9.5, 6.4 Hz, 1H), 3.52 (m, 1H), 3.02 (s, 2H), 2.78-2.60 (m, 4H), 2.58 (d, J=7.1 Hz, 2H), 1.95 (m, 2H), 1.85 (m, 2H).

APCI-MS: m/z 424 (MH$^+$).

Example 17

5-Chloro-2-[2-chloro-3-(5-chloro-1'H,3H-spiro[1-benzofuran-2,4'-piperidin]-1'-yl)propoxy]-4hydroxybenzoic acid Step I:

Methyl 5-chloro-2,4-dihydroxybenzoate

Prepared from methyl 2,4-dihydroxybenzoate using the procedure described by Anderson, W. K., et al.,*J. Med. Chem.* 1996, 39, 46-55.

$^1$H-NMR (CDCl$_3$, 400 MHz): δ 10.85 (s, 1H), 7.84 (s, 1H), 6.63 (s, 1H), 5.99 (s, 1H), 3.95 (s, 3H)

Step II:

Methyl 5-chloro-2-hydroxy-4-[(4-methoxybenzyl)oxy]benzoate

To a solution of methyl 5-chloro-2,4-dihydroxybenzoate (0.41 g, 2 mmol) in acetone were added 1-(chloromethyl)-4-methoxybenzene (0.32 g, 2 mmol) and K$_2$CO$_3$ (0.28 g, 2 mmol). The reaction mixture was heated with reflux for 3 days, than cooled to room temperature. The inorganic material was removed by filtration. The solvent was distilled in vacuo, and the residue was recrystallized from methanol to afford white solid (0.37 g, 60%).

$^1$H-NMR (CDCl$_3$, 400 MHz): δ 10.89 (s, 1H), 7.82 (s, 1H), 7.37 (d, J=8.7 Hz, 2H), 6.92 (d, J=8.7 Hz, 2H), 6.56 (s, 1H), 5.09 (s, 2H), 3.92 (s, 3H), 3.82 (s, 3H)

Step III:

Methyl 5-chloro-4-[(4-methoxybenzyl)oxy]-2-[(2S)-oxiran-2-ylmethoxy]benzoate

A solution of methyl 5-chloro-2-hydroxy-4-[(4-methoxybenzyl)oxy]benzoate (0.37 g, 1.16 mmol), (2S)-oxiran-2-ylmethyl 3-nitrobenzenesulfonate (0.30 g, 1.16 mmol) and caesium carbonate (0.45 g, 1.4 mmol) in dimethylformamide (15 mL) was stirred at room temperature overnight. The mixture was partitioned between water and ethyl acetate, and the organic phase was washed twice with water and once with brine, and finally concentrated. The crude material was purified by flash chromatography on silica gel (eluent: ethyl acetate/n-heptane), yielding the titled compound (0.33, 74%).

$^1$H-NMR (CDCl$_3$, 400 MHz): δ 7.91 (s, 1H), 7.37 (d, J=8.7 Hz, 2H), 6.92 (dd, J=6.7, 2.0 Hz, 2H), 6.66 (s, 1H), 5.14 (m, 2H), 4.33 (dd, J=11.4, 2.6 Hz, 1H), 3.98 (dd, J=11.5, 5.1 Hz, 1H), 3.86 (s, 3H), 3.82 (s, 3H), 3.36 (m, 1H), 2.93-2.87 (m, 2H)

APCI-MS: m/z 379 (MH$^+$)

Step IV

Methyl 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoate trifluoroacetate (salt)

A solution of 5-chloro-3H-spiro[1-benzofuran-2,4'-piperidine] (100 mg, 0.45 mmol) and methyl 5-chloro-4-[(4-methoxybenzyl)oxy]-2-[(2S)-oxiran-2-ylmethoxy]benzoate (170 mg, 0.45 mmol) in ethanol (5 mL) was refluxed for 6 h. The solvent was distilled off under reduced pressure. The residue was purified by HPLC (eluent: [acetonitrile/water+0.1% TFA]) to afford a colourless solid (218 mg, 67%).

APCI-MS: m/z 602 (MH$^+$)

Step V:

5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride To a mixture of methyl 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoate trifluoroacetate salt (220 mg, 0.3 mmol) in ethanol (10 mL) was added a solution of potassium hydroxide (4 g) and water (4 mL). The mixture was stirred at room temperture for 3 hours, pH was adjusted to 1 with aqueous HCl (37%), extracted with ethyl acetate, dried with sodium sulphate. Volatiles was removed in vacuo, the subtitle compound (180 mg) required no further purification.

APCI-MS: m/z 588 (MH$^+$)

Step VI:

5-chloro-2-[2-chloro-3-(5-chloro-1'H,3H-spiro[1-benzofuran-2,4'-piperidin]-1'-yl)propoxy]-4-[(4-methoxybenzyl)oxy]benzoic acid To a stirred suspension of 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (0.623 g, 1 mmol) in dry THF (50 ml) was added thionyl chloride (0.187 g, 1.5 mmol). The reaction mixture was stirred at room temperature overnight, then quenched with water (100 ml), and extracted with ethyl acetate (3×75 ml). The combined organic extracts were dried over Na$_2$SO$_4$, and the solvent was removed i.vac. The residue was purified by HPLC (eluent: [acetonitrile/water+0.1% TFA]) to afford the subtitle compound as trifluoroacetate salt (134 mg, 19%).

APCI-MS: m/z 608 (MH$^+$)

Step VII:

5-Chloro-2-[2-chloro-3-(5-chloro-1'H,3H-spiro[1-benzofuran-2,4'-piperidin]-1'-yl)propoxy]-4-hydroxybenzoic acid To a solution of 5-chloro-2-[2-chloro-3-(5-chloro-1'H,3H-spiro[1-benzofuran-2,4'-piperidin]-1'-yl)propoxy]-4-[(4-methoxybenzyl)oxy]benzoic acid trifluoroacetate salt (45 mg, 0.062 mmol) in DCM (2 ml) was added trifluoroacetic acid (95% in water, 1 ml), and the reaction mixture was stirred at room temperature for 2 h. The solvent was removed i.vac, the residue purified by HPLC (eluent: [acetonitrile/water+0.1% TFA]) to afford the title compound as trifluoroacetate salt (25 mg, 67%).

$^1$H-NMR (400 MHz, acetone-d6): δ 7.91 (s, 1H), 7.22 (m, 1H), 7.13 (m, 2H), 6.76 (d, J=8.5 Hz, 1H), 5.08 (tt, J=7.3, 4.8 Hz, 1H), 4.62 (dd, J=9.8, 4.8 Hz, 1H), 4.35 (dd, J=9.7, 7.3 Hz, 1H), 4.09 (dd, J=13.8, 7.4 Hz, 1H), 3.90 (dd, J=13.7, 4.6 Hz, 2H), 3.75 (m, 1H), 3.61 (m, 2H), 3.20 (s, 2H), 2.50 (m, 2H), 2.23 (m, 2H)

APCI-MS: m/z 488 (MH$^+$)

Example 18

2-[2-Amino-3-(5-chloro-1'H,3H-spiro[1-benzofuran-2,4'-piperidin]-1'-yl)propoxy]-5-chloro-4-hydroxybenzoic acid 5-Chloro-2-[2-chloro-3-(5-chloro-1'H,3H-spiro[1-benzofuran-2,4'-piperidin]-1'-yl)propoxy]-4-[(4-methoxybenzyl)oxy]benzoic acid trifluoroacetate salt (see Example 17, Step VI) (35 mg, 0.048 mmol) was dissolved in a solution of NH$_3$ in methanol (7 M, 1 ml) and stirred at room temperature for 3 days. The volatiles were removed i.vac., the residue dissolved in DCM (1 ml), and TFA (95% in water, 0.5 ml) was added. The solution was stirred at room temperature for 2 h, then the solvent was removed i.vac. The residue was purified by HPLC (eluent: [acetonitrile/water+0.1% TFA]) to afford the title compound as bistrifluoroacetate salt (15 mg, 44%).

$^1$H-NMR (400 MHz, acetone-d$_6$): δ 7.90 (s, 1H), 7.16 (d, J=2.0 Hz, 1H), 7.10 (s, 1H), 7.08 (dd, J=8.5, 2.3 Hz, 1H), 6.70 (d, J=8.5 Hz, 1H), 4.53 (dd, J=10.7, 3.2 Hz, 1H), 4.35 (dd, J=10.6, 4.6 Hz, 1H), 3.66-3.48 (m, 3H), 3.23-3.03 (m, 4H), 2.94 (m, 1H), 2.83 (m, 1H), 2.12-1.94 (m, 4H, partially covered with the signal of the solvent).

APCI-MS: m/z 467 (MH$^+$)

Example 19

5-chloro-2-[3-(5-chloro-1'H,3H-spiro[1-benzofuran-2,4'-piperidin]-1'-yl)-2-(methylamino)propoxy]-4hydroxybenzoic acid 5-Chloro-2-[2-chloro-3-(5-chloro-1'H,3H-spiro[1-benzofuran-2,4'-piperidin]-1'-yl)propoxy]-4-[(4-methoxybenzyl)oxy]benzoic acid trifluoroacetate salt (see Example 17, Step VI) (35 mg, 0.048 mmol) was dissolved in a solution of methylamine in ethanol (33 % wt., 1 ml) and stirred at room temperature for 3 days, then at 40° C. for 24 h. The volatiles were removed i.vac., the residue dissolved in DCM (1 ml), and TFA (95% in water, 0.5 ml) was added. The solution was stirred at room temperature for 2 h, then the solvent was removed i.vac. The residue was purified by HPLC (eluent: [acetonitrile/water+0.1% TFA]) to afford the title compound as bistrifluoroacetate salt (24 mg, 70%).

$^1$H-NMR (400 MHz, acetone-d$_6$): δ 7.92 (s, 1H), 7.29 (s, 1H), 7.17 (d, J=2.0 Hz, 1H), 5 7.09 (dd, J=8.5, 2.3 Hz, 1H), 6.72 (d, J=8.4 Hz, 1H), 4.61 (d, J=6.0 Hz, 2H), 3.98 (m, 1H), 3.83 (dd, J=13.0, 4.1 Hz, 1H), 3.73 (dd, J=13.1, 6.9 Hz, 1H), 3.40-3.22 (m, 4H), 3.11 (s, 2H), 2.93 (s, 3H), 2.13-2.03 (m, 4H, partially covered with the signal of solvent).

APCI-MS: m/z 481 (MH$^+$)

Example 20

5-chloro-2-[3-(5-chloro-1'H,3H-spiro[1-benzofuran-2,4'-piperidin]-1'-yl)-2-(dimethylamino)propoxy]-4-hydroxybenzoic acid 5-Chloro-2-[2-chloro-3-(5-chloro-1'H,3H-spiro[1-benzofuran-2,4'-piperidin]-1'-yl)propoxy]-4-[(4-methoxybenzyl)oxy]benzoic acid trifluoroacetate salt (see Example 17, Step VI) (35 mg, 0.048 mmol) was dissolved in a solution of dimethylamine in ethanol (33 % wt., 1 ml) and stirred at room temperature for 3 days, then at 40° C. for 36 h. The volatiles were removed i.vac., the residue dissolved in DCM (1 ml), and TFA (95% in water, 0.5 ml) was added. The solution was stirred at room temperature for 2 h, then the solvent was removed i.vac. The residue was purified by HPLC (eluent: [acetonitrile/water+0.1% TFA]) to afford the title compound as bistrifluoroacetate salt (19 mg, 54%).

$^1$H-NMR (400 MHz, acetone-$d_6$): δ 7.90 (s, 1H), 7.37 (s, 1H), 7.16 (d, J=2.0 Hz, 1H), 7.08 (dd, J=8.5, 2.3 Hz, 1H), 6.69 (d, J=8.4 Hz, 1H), 4.49 (dd, J=9.9, 5.2 Hz, 2H), 4.43 (dd, J=9.7, 7.2 Hz, 2H), 3.85 (m, 1H), 3.76 (m, 2H), 3.16 (s, 6H), 3.20-2.86 (m, 6H), 2.01-1.86 (m, 4H).

APCI-MS: m/z 495 (MH$^+$)

THP-1 Chemotaxis Assay

Introduction

The assay measures the chemotactic response elicited by MIP-1α chemokine in the human monocytic cell line THP-1. Compounds are evaluated by their ability to depress the chemotactic response to a standard concentration of MIP-1α chemokine.

Methods

Culture of THP-1 Cells

Cells are thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+10% HIFCS). At day 3 the medium is discarded and replaced with fresh medium.

THP-1 cells are routinely cultured in RPMI-1640 medium supplemented with 10% heat inactivated fetal calf serum and glutamax but without antibiotics. Optimal growth of the cells requires that they are passaged every 3 days and that the minimum subculture density is 4×10$^5$ cells/ml.

Chemotaxis Assay

Cells are removed from the flask and washed by centrifugation in RPMI+10% HIFCS+glutamax. The cells are then resuspended at 2×10cells/ml in fresh medium (RPMI+10% HIFCS+glutamax) to which is added calcein-AM (5 μl of stock solution to 1 ml to give a final concentration of 5×10$^{-6}$ M). After gentle mixing the cells are incubated at 37° C. in a CO$_2$ incubator for 30 minutes. The cells are then diluted to 50 ml with medium and washed twice by centrifugation at 400× g. Labelled cells are then resuspended at a cell concentration of 1×10$^7$ cells/ml and incubated with an equal volume of MIP-1α antagonist (10$^{-10}$ M to 10$^{-6}$ M final concentration) for 30 minutes at 37° C. in a humidified CO$_2$ incubator.

Chemotaxis is performed using Neuroprobe 96-well chemotaxis plates employing 8 μm filters (cat no. 101-8). Thirty microlitres of chemoattractant supplemented with various concentrations of antagonists or vehicle are added to the lower wells of the plate in triplicate. The filter is then carefully positioned on top and then 25 μl of cells preincubated with the corresponding concentration of antagonist or vehicle is added to the surface of the filter. The plate is then incubated for 2 hours at 37° C. in a humidified CO$_2$ incubator. The cells remaining on the surface are then removed by adsorption and the whole plate is centrifuged at 2000 rpm for 10 minutes. The filter is then removed and the cells that have migrated to the lower wells are quantified by the fluorescence of cell associated calcein-AM. Cell migration is then expressed in fluorescence units after subtraction of the reagent blank and values are standardized to % migration by comparing the fluorescence values with that of a known number of labelled cells. The effect of antagonists is calculated as % inhibition when the number of migrated cells is compared with vehicle.

The invention claimed is:

1. A compound of formula

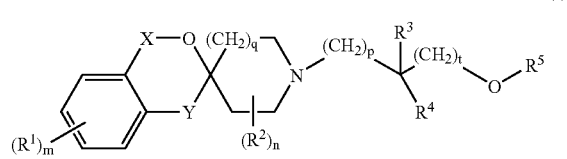

(I)

wherein m is 0, 1, 2, 3 or 4;

each R$^1$ independently represents halogen, cyano, hydroxyl, C$_1$-C$_6$ alkyl, C$_1$-C$_6$ haloalkyl, C$_1$-C$_6$ alkoxy, C$_1$-C$_6$ alkylsulphonyl or sulphonamido (—SO$_2$NH$_2$);

X represents a bond or —CH$_2$— and Y represents a bond or —CH$_2$—, provided that X and Y do not both simultaneously represent a bond or —CH$_2$—;

n is 0, 1 or 2;

each R$^2$ independently represents halogen, C$_1$-C$_6$ alkyl or C$_1$-C$_6$ haloalkyl;

q is 0 or 1;

p is 0, 1 or 2;

R$^3$ represents a group selected from halogen, NR$^6$R$^7$, carboxyl or C$_1$-C$_6$ alkyl wherein said C$_1$-C$_6$ alkyl group is optionally substituted by one or more halogen, amino, hydroxyl, C$_1$-C$_6$ alkoxy, N-(C$_1$-C$_6$ alkyl)amino, N,N-di-(C$_1$-C$_6$ alkyl)amino, carboxy or carbamoyl;

R$^4$ represents hydrogen, C$_1$-C$_6$ alkyl, C$_1$-C$_6$ haloalkyl or halogen;

t is 0, 1 or 2, provided that p and t are not both 0;

R$^5$ represents a saturated or unsaturated 5- to 10-membered ring system which ring system may comprise at least one ring heteroatom selected from nitrogen, oxygen and sulphur, the ring system being optionally substituted by one or more substituents independently selected from halogen, cyano, oxo, nitro, hydroxyl, carboxyl, —C(O)H, —NR$^8$R$^9$, —C(O)NR$^{10}$R$^{11}$, —NHC(O)R$^{12}$, —NHSO$_2$R$^{13}$, —SO$_2$NR$^{14}$R$^{15}$, —NHC(O)NR$^{16}$R$^{17}$, a group selected from C$_1$-C$_6$ alkyl, C$_2$-C$_6$ alkenyl, C$_2$-C$_6$ alkynyl, C$_1$-C$_6$ alkoxy, C$_1$-C$_6$ alkylthio, C$_1$-C$_6$ alkylsulphonyl, C$_1$-C$_6$ haloalkyl, C$_1$-C$_6$ alkylcarbonyl, phenylcarbonyl, C$_3$-C$_6$ cycloalkyl, phenyl and a saturated or unsaturated 5- to 6-membered heterocyclic ring comprising at least one ring heteroatom selected from nitrogen, oxygen and sulphur, each group being optionally substituted by one or more substituents independently selected from halogen, cyano, hydroxyl, carboxyl, C$_1$-C$_6$ alkyl, C3-C6 cycloalkyl, C$_1$-C$_6$ alkoxy and C$_1$-C$_6$ alkoxycarbonyl;

R$^6$ and R$^7$ each independently represent hydrogen or a group selected from C$_1$-C$_6$ alkyl and C$_1$-C$_6$ alkylcarbonyl, each of which may be optionally substituted by one or more substituents selected from halogen, amino, hydroxyl, C$_1$-C$_6$ alkoxy, N-( C$_1$-C$_6$ alkyl)amino, N,N-di-(C$_1$-C$_6$ alkyl)amino, carboxy, carbamoyl or C$_1$-C$_6$ alkoxycarbonyl, or R6 and R7 together with the nitrogen atom to which they are attached form a 4- to 7-membered saturated heterocyclic ring which may be optionally substituted by one or more substituent selected from halogen, amino, hydroxyl, C$_1$-C$_6$ alkoxy, N-( C$_1$-C$_6$ alkyl)amino, N,N-di-($C_1$-$C_6$ alkyl)amino, carboxy, carbamoyl or $C_1$-$C_6$ alkoxycarbonyl;

$R^8$, $R^9$, $R^{10}$, $R^{11}$ each independently represent hydrogen or a group selected from $C_1$-$C_6$ alkyl or $C_3$-$C_6$ cycloalkyl, each group being optionally substituted by one or more substituents independently selected from halogen, amino, hydroxyl, $C_1$-$C_6$ alkoxy, N-($C_1$-$C_6$ alkyl)amino, N,N-di-($C_1$-$C_6$ alkyl)amino, carboxy or carbamoyl; or $R^{10}$ and $R^{11}$, together with the nitrogen atom to which they are attached form a 4- to 7-membered saturated heterocyclic ring which may be optionally substituted with at least one substituent selected from halogen, amino, hydroxyl, $C_1$-$C_6$ alkoxy, N-($C_1$-$C_6$ alkyl)amino, N,N-di-($C_1$-$C_6$ alkyl)amino, carboxy or carbamoyl;

$R^{12}$ represents hydrogen or a group selected from $C_1$-$C_6$ alkyl or $C_3$-$C_6$ cycloalkyl, each group being optionally substituted by one or more substituents independently selected from halogen, amino, hydroxyl, $C_1$-$C_6$ alkoxy, N-($C_1$-$C_6$ alkyl)amino, N,N-di-($C_1$-$C_6$ alkyl)amino, carboxy or carbamoyl;

$R^{13}$ represents a group selected from $C_1$-$C_6$ alkyl or $C_3$-$C_6$ cycloalkyl, each group being optionally substituted by one or more substituents independently selected from halogen, amino, hydroxyl, $C_1$-$C_6$ alkoxy, N-($C_1$-$C_6$ alkyl)amino, N,N-di-($C_1$-$C_6$ alkyl)amino, carboxy or carbamoyl;

$R^{14}$, $R^{15}$, $R^{16}$ and $R^{17}$ each independently represent hydrogen or a group selected from $C_1$-$C_6$ alkyl or $C_3$-$C_6$ cycloalkyl, each group being optionally substituted by one or more substituents independently selected from halogen, amino, hydroxyl, $C_1$-$C_6$ alkoxy, N-($C_1$-$C_6$ alkyl)amino, N,N-di-($C_1$-$C_6$ alkyl)amino, carboxy or carbamoyl; or $R^{14}$ and $R^{15}$, or $R^{16}$ and $R^{17}$, together with the nitrogen atom to which they are attached each independently form a 4- to 7-membered saturated heterocyclic ring which may be optionally substituted with at least one substituent selected from halogen, amino, hydroxyl, $C_1$-$C_6$ alkoxy, N-($C_1$-$C_6$ alkyl)amino, N,N-di-($C_1$-$C_6$ alkyl)amino, carboxy or carbamoyl;

or a pharmaceutically acceptable salt thereof.

2. A compound according to claim 1 wherein X represents a bond and Y represents —$CH_2$—.

3. A compound according to claim 1 wherein q is 1.

4. A compound according to claim 1 wherein m is 0 or 1 and $R^1$ represents halogen.

5. A compound according to claim 1 wherein n is 0.

6. A compound according to claim 1 wherein $R^3$ represents halogen, —$NR^6R^7$ or $C_1$-$C_6$ alkyl optionally substituted by one or two substituents selected from halogen, amino or hydroxyl.

7. A compound according to claim 1 wherein $R^4$ represents hydrogen.

8. A compound according to claim 1 wherein $R^5$ represents a saturated or unsaturated 5- to 10-membered ring system which ring system may comprise one, two, three or four ring heteroatoms independently selected from nitrogen, oxygen and sulphur and which may be optionally substituted one two or three substituents independently selected from halogen, cyano, oxo, nitro, hydroxyl, carboxyl, —C(O)H, —$NR^8R^9$, —C(O)$NR^{10}R^{11}$, —NHC(O)$R^{12}$, —$NHSO_2R^{13}$, —$SO_2NR^{14}R^{15}$, —NHC(O)$NR^{16}R^{17}$, a group selected from $C_1$-$C_6$ alkyl, $C_2$-$C_6$ alkenyl, $C_2$-$C_6$ alkynyl, $C_1$-$C_6$ alkoxy, $C_1$-$C_6$ alkylthio, $C_1$-$C_6$ allylsulphonyl, $C_1$-$C_6$ haloalkyl, $C_1$-$C_6$ alkylcarbonyl, phenylcarbonyl, $C_3$-$C_6$ cycloalkyl, phenyl and a saturated or unsaturated 5- to 6-membered heterocyclic ring comprising at least one ring heteroatom selected from nitrogen, oxygen and sulphur, each group being optionally substituted by one or more substituents independently selected from halogen, cyano, hydroxyl, carboxyl, $C_1$-$C_6$ alkyl, $C_1$-$C_6$ cycloalkyl, $C_1$-$C_6$ alkoxy and $C_1$-$C_6$ alkoxycarbonyl.

9. A claim according to claim 1 wherein $R^5$ represents phenyl, wherein said phenyl is optionally substituted with one or two substituents independently selected from —NHC(O)$R^{12}$, —NHC(O)$NR^{16}R^{17}$, hydroxyl or $C_1$-$C_6$ alkoxy, or wherein said phenyl is optionally substituted with one, two or three substituents independently selected from halogen, hydroxyl, or carboxyl.

10. A compound according to claim 1 selected from:

N-(2-{[(2S)-2-amino-3-(5-chloro-1'H,3H-spiro[1-benzofuran-2,4'-piperidin]-1'-yl)propyl]oxy}-4-methoxyphenyl)acetamide;

N-(2-{[(2S)-2-amino-3-(5-chloro-1'H,3H-spiro[1-benzofuran-2,4'-piperidin]-1'-yl)propyl]oxy}-4-hydroxyphenyl)acetamide bis(trifluoroacetate) (salt);

N-(2-{[(2S)-2-amino-3-(5-fluoro-1'H,3H-spiro[1-benzofuran-2,4'-piperidin]-1'-yl)propyl]oxy}-4-methoxyphenyl)acetamide;

N-(2-{[(2S)-2-amino-3-(5-fluoro-1'H,3H-spiro[1-benzofuran-2,4'-piperidin]-1'-yl)propyl]oxy}-4-hydroxyphenyl)acetamide bis(trifluoroacetate) (salt);

N-(2-{[(2S)-2-Amino-3-(1'H,3H-spiro[1-benzofuran-2,4'-piperidin]-1'-yl)propyl]oxy}-4-methoxyphenyl)acetamide;

N-(2-{[(2S)-2-Amino-3-(1'H,3H-spiro[1-benzofuran-2,4'-piperidin]-1'-yl)propyl]oxy}-4-hydroxyphenyl)acetamide bis(trifluoroacetate) (salt);

N-(2-{[(2S)-2-(Acetylamino)-3-(5-fluoro-1'H,3H-spiro[1-benzofuran-2,4'-piperidin]-1'-yl)propyl]oxy}-4-methoxyphenyl)acetamide;

N-{2-[3-Amino-2-(5-chloro-1'H,3H-spiro[1-benzofuran-2,4'-piperidin]-1'-yl)propoxy]-4-methoxyphenyl}acetamide bis(trifluoroacetate);

N-{2-[3-Amino-2-(5-fluoro-1'H,3H-spiro[1-benzofuran-2,4'-piperidin]-1'-yl)propoxy]-4-methoxyphenyl}acetamide bis(trifluoroacetate);

N-{2-[3-Amino-2-(1'H,3H-spiro[1-benzofuran-2,4'-piperidin]-1'-yl)propoxy]-4-methoxyphenyl}acetamide bis(trifluoroacetate);

N-{2-[3-Amino-2-(5-chloro-1'H,3H-spiro[1-benzofuran-2,4'-piperidin]-1'-yl)propoxy]phenyl}urea bis(trifluoroacetate);

N-{2-[3-Amino-2-(5-fluoro-1'H,3H-spiro[1-benzofuran-2,4'-piperidin]-1'-yl)propoxy]phenyl}urea bis(trifluoroacetate);

N-{2-[2-Chloro-3-(5-chloro-1'H,3H-spiro[1-benzofuran-2,4'-piperidin]-1'-yl)propoxy]-4-hydroxyphenyl}acetamide trifluoroacetate (salt);

N-{2-[2-(5-Chloro-1'H,3H-spiro[1-benzofuran-2,4'-piperidin]-1'-yl)propoxy]-4-methoxyphenyl}acetamide trifluoroacetate;

5-{[(2S)-2-Amino-3-(5-fluoro-1'H,3H-spiro[1-benzofuran-2,4'-piperidin]-1'-yl)propyl]oxy}-2H-1,4-benzoxazin-3(4H)-one;

8-{[(2S)-2-Amino-3-(5-fluoro-1'H,3H-spiro[1-benzofuran-2,4'-piperidin]-1'-yl)propyl]oxy}quinolin-2(1H)-one;

5-Chloro-2-[2-chloro-3-(5-chloro-1'H,3H-spiro[1-benzofuran-2,4'-piperidin]-1'-yl)propoxy]-4-hydroxybenzoic acid;

2-[2-Amino-3-(5-chloro-1'H,3H-spiro[1-benzofuran-2,4'-piperidin]-1'-yl)propoxy]-5-chloro-4-hydroxybenzoic acid;

5-chloro-2-[3-(5-chloro-1'H,3H-spiro[1-benzofuran-2,4'-piperidin]-1'-yl)-2-(methylamino)propoxy]-4-hydroxybenzoic acid;

5-chloro-2-[3-(5-chloro-1'H,3H-spiro[1-benzofuran-2,4'-piperidin]-1'-yl)-2-(dimethylamino)propoxy]-4-hydroxybenzoic acid and pharmaceutically acceptable salts of any one thereof.

11. A process for the preparation of a compound of formula (I) as defined in claim 1 or a pharmaceutically acceptable salt thereof which comprises:

(a) converting a compound of formula (II)

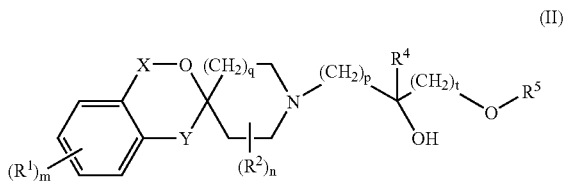

wherein $R^1$, m, X, Y, $R^2$, n, q, p, $R^4$, t and $R^5$ are as defined in formula (I), into a compound of formula (I); or (b) reacting a compound of formula (III)

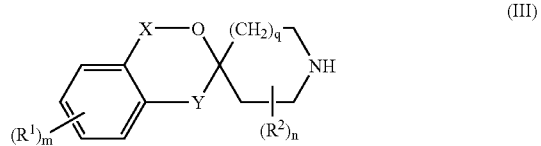

wherein $R^1$, m, X, y, $R^2$, n and q are as defined for formula (I), with a compound of formula (IV)

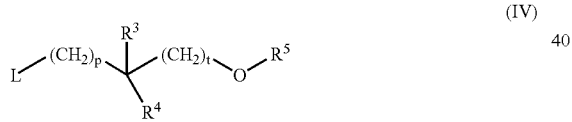

wherein L is a leaving group and p, $R^3$, $R^4$, t and $R^5$ are as defined for formula (I);

(c) reacting a compound of formula (V)

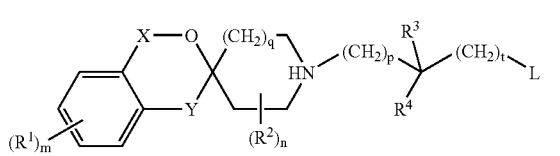

wherein $R^1$, m, X, Y, $R^2$, n, q, p, , $R^3$, $R^4$ and t are as defined for formula (I), with a compound of formula (VI)

wherein L is a leaving group and $R^5$ is as defined for formula (I);

and optionally thereafter if necessary:

(i) converting a compound of formula (I) into another compound of formula (I);

(ii) removing any protecting groups; or (iii) forming a pharmaceutically acceptable salt.

12. A pharmaceutical composition comprising a compound of formula (I) or a pharmaceutically acceptable salt thereof as claimed in claim 1 in associated with a pharmaceutically acceptable adjuvant, diluent or carrier.

13. A process for the preparation of a pharmaceutical composition comprising a compound of formula (I) or a pharmaceutically acceptable salt thereof as claimed in claim 1, in association with a pharmaceutically acceptable adjuvant, diluent or carrier, the process comprising mixing a compound of formula (I) or a pharmaceutically acceptable salt thereof with a pharmaceutically acceptable adjuvant, diluent or carrier.

14. A method of treating rheumatoid arthritis, the method comprising administering to a patient in need thereof a therapeutically effective amount of a compound of formula (I) or a pharmaceutically acceptable salt thereof as claimed in claim 1.

15. A method of treating multiple sclerosis, the method comprising administering to a patient in need thereof a therapeutically effective amount of a compound of formula (I) or a pharmaceutically acceptable salt thereof as claimed in claim 1.

16. The method of claim 14
wherein
m is 0 or 1;
each $R^1$ independently represents halogen;
X represents a bond and Y represents —$CH_2$;
n is 0;
q is 1;
p is 0 or 1;
$R^3$ represents a group selected from halogen, $NR^6R^7$ or $C_1$-$C_6$ alkyl wherein said $C_1$-$C_6$ alkyl group is optionally substituted by one amino, hydroxyl, $C_1$-$C_6$ alkoxy, N-($C_1$-$C_6$ alkyl)amino, N,N-di-($C_1$-$C_6$ alkyl)amino, carboxy or carbamoyl;
$R^4$ hydrogen;
t is 0 or 1, provided that p and t are not both 0;
$R^5$ represents phenyl, benzoxazinone or quinolinone, the ring system being optionally substituted by one or more substituents independently selected from halogen, hydroxyl, carboxyl, —NHC(O)$R^{12}$, —NHC(O)N$R^{16}R^{17}$, or $C_1$-$C_6$alkoxy;
$R^6$ and $R^7$ each independently represent hydrogen or a group selected from $C_1$-$C_6$ alkyl and $C_1$-$C_6$ alkylcarbonyl;
$R^8$, $R^9$, $R^{10}$, $R^{11}$ each independently represent hydrogen or a group selected from $C_1$-$C_6$ alkyl or $C_3$-$C_6$ cycloalkyl;
$R^{12}$ represents hydrogen or a group selected from $C_1$-$C_6$ alkyl;
$R^{16}$ and $R^{17}$ each independently represent hydrogen;
or a pharmaceutically acceptable salt thereof.

17. The method of claim 15
wherein
m is 0 or 1;
each $R^1$ independently represents halogen;
X represents a bond and Y represents —$CH_2$;
n is 0;
q is 1;
p is 0 or 1;
$R^3$ represents a group selected from halogen, $NR^6R^7$ or $C_1$-$C_6$ alkyl wherein said $C_1$-$C_6$ alkyl group is optionally substituted by one amino, hydroxyl, $C_1$-$C_6$ alkoxy, N-($C_1$-$C_6$ alkyl)amino, N,N-di-($C_1$-$C_6$ alkyl)amino, carboxy or carbamoyl;
$R^4$ represents hydrogen;

t is 0 or 1, provided that p and t are not both 0;

$R^5$ represents phenyl, benzoxazinone or quinolinone, the ring system being optionally substituted by one or more substituents independently selected from halogen, hydroxyl, carboxyl, —NHC(O)$R^{12}$, —NHC(O)N$R^{16}R^{17}$, or $C_1$-$C_6$alkoxy;

$R^6$ and $R^7$ each independently represent hydrogen or a group selected from $C_1$-$C_6$ alkyl and $C_1$-$C_6$ alkylcarbonyl;

$R^8$, $R^9$, $R^{10}$, $R^{11}$ each independently represent hydrogen or a group selected from $C_1$-$C_6$ alkyl or $C_3$-$C_6$ cycloalkyl;

$R^{12}$ represents hydrogen or a group selected from $C_1$-$C_6$ alkyl;

$R^{16}$ and $R^{17}$ each independently represent hydrogen;

or a pharmaceutically acceptable salt thereof.

* * * * *

UNITED STATES PATENT AND TRADEMARK OFFICE
CERTIFICATE OF CORRECTION

PATENT NO. : 7,524,856 B2  Page 1 of 1
APPLICATION NO. : 10/583468
DATED : April 28, 2009
INVENTOR(S) : Nafizal Hossain and Svetlana Ivanova It is certified that error appears in the above-identified patent and that said Letters Patent is hereby corrected as shown below:

Title page;

Face of Patent, right hand column, "Haolgen" should read -- Halogen --.

Face of Patent, right hand column, Ting et al., "Antagonist" should read -- Antagonists --.

Title page; Item (57) Face of Patent, line 2 of Abstract, "and," should read -- and --.

Column 36, line 55, "C3-C6" should read -- $C_3$-$C_6$ --.

Column 36, line 63, "R6 and R7" should read -- $R^6$ and $R^7$ --.

Column 37, line 57, "one two" should read -- one, two --.

Column 37, line 63, "allylsulphonyl," should read -- alkylsulphonyl, --.

Column 38, line 14, "1'- yl)" should read -- 1'-yl) --.

Column 39, line 35, "y," should read -- Y, --.

Column 39, line 59, "p, ," should read -- p, --.

Column 40, line 5, "associated" should read -- association --.

Column 40, line 38, "$R^4$" should read -- $R^4$ represents --.

Signed and Sealed this

Thirtieth Day of November, 2010

David J. Kappos
*Director of the United States Patent and Trademark Office*